US012648968B2

(12) United States Patent
Ichim

(10) Patent No.: US 12,648,968 B2
(45) Date of Patent: Jun. 9, 2026

(54) FIBROBLAST AND FIBROBLAST-IMMUNOCYTE COMBINATIONS FOR TREATMENT OF SUBCONCUSSIVE- AND CONCUSSIVE-ASSOCIATED NEUROLOGICAL DAMAGE

(71) Applicant: SPINALCYTE LLC, Houston, TX (US)

(72) Inventor: Thomas Ichim, San Diego, CA (US)

(73) Assignee: SPINALCYTE LLC, Houston, TX (US)

(*) Notice: Subject to any disclaimer, the term of this patent is extended or adjusted under 35 U.S.C. 154(b) by 809 days.

(21) Appl. No.: 17/753,491

(22) PCT Filed: Sep. 9, 2020

(86) PCT No.: PCT/US2020/049949
§ 371 (c)(1),
(2) Date: Mar. 4, 2022

(87) PCT Pub. No.: WO2021/050549
PCT Pub. Date: Mar. 18, 2021

(65) Prior Publication Data
US 2022/0339201 A1      Oct. 27, 2022

Related U.S. Application Data

(60) Provisional application No. 62/897,428, filed on Sep. 9, 2019.

(51) Int. Cl.

| | |
|---|---|
| *A61K 35/33* | (2015.01) |
| *A61K 35/15* | (2025.01) |
| *A61K 35/28* | (2015.01) |
| *A61K 38/17* | (2006.01) |
| *A61P 25/00* | (2006.01) |

(52) U.S. Cl.
CPC .............. *A61K 35/33* (2013.01); *A61K 35/15* (2013.01); *A61K 35/28* (2013.01); *A61K 38/177* (2013.01); *A61P 25/00* (2018.01)

(58) Field of Classification Search
None
See application file for complete search history.

(56) References Cited

U.S. PATENT DOCUMENTS

| | | | |
|---|---|---|---|
| 5,188,817 A | 2/1993 | Ozick | |
| 7,569,385 B2 | 8/2009 | Haas | |
| 7,850,983 B2 | 12/2010 | Sevrain et al. | |
| 9,173,906 B2 | 11/2015 | Rolland et al. | |
| 9,603,878 B2 | 3/2017 | Berry et al. | |
| 10,987,325 B2 | 4/2021 | Bradley et al. | |
| 11,034,934 B2 | 6/2021 | O'Heeron et al. | |
| 11,819,555 B2 | 11/2023 | O'Heeron | |
| 2002/0037279 A1 | 3/2002 | Vandenburgh | |
| 2004/0107453 A1 | 6/2004 | Furcht et al. | |
| 2005/0147596 A1 | 7/2005 | Keller et al. | |
| 2005/0170510 A1 | 8/2005 | Huang et al. | |
| 2006/0233766 A1 | 10/2006 | Messina et al. | |
| 2009/0202500 A1 | 8/2009 | Tamai et al. | |
| 2014/0314726 A1 | 10/2014 | O'Heeron et al. | |
| 2016/0375098 A1 | 12/2016 | Kadouri et al. | |
| 2017/0224740 A1* | 8/2017 | Sing et al. ............. A61K 35/48 | |
| 2017/0281685 A1 | 10/2017 | Bogin et al. | |
| 2018/0071342 A1 | 3/2018 | Ichim et al. | |
| 2018/0133258 A1 | 5/2018 | Ichim et al. | |
| 2018/0195044 A1 | 7/2018 | O'Heeron et al. | |
| 2019/0101547 A1* | 4/2019 | Berger et al. ...... G01N 33/6893 | |
| 2019/0136299 A1 | 5/2019 | Putignani et al. | |

FOREIGN PATENT DOCUMENTS

| | | |
|---|---|---|
| JP | H06502406 A | 3/1994 |
| JP | 2018-511599 | 4/2018 |
| WO | WO 1992/006702 | 4/1992 |
| WO | WO-2005017117 A2 | 2/2005 |
| WO | WO-2007035843 A2 | 3/2007 |
| WO | WO-2007149548 A2 | 12/2007 |

(Continued)

OTHER PUBLICATIONS

Cox Jr. et al. "Treatment of sever adult traumatic brain injury using bone marrow mononuclear cells" Stem Cells (Year: 2016).*

Feng-Juan Lv et al. "Concise Review: the surface markers and identity of human mesenchymal stem cells" Stem Cells (Year: 2014).*

Kahounova et al. "The fibroblast surface markers FAP, anti-Fibroblast, and FSP are expressed by cells of epithelial origin and may be altered during epithelial to mesenchymal transition" Cytometry Part A (Year: 2017).*

Li et al., "Conversion of astrocytes and fibroblasts into functional noradrenergic neurons" Cell Reports (Year: 2019).*

Maleki et al. "Comparison of mesenchymal stem cell markers in multiple human adult stem cells" Int J. Stem Cells (Year: 2014).*

Narayan et al., "Oct4 and Sox2 work as transcriptional activators in reprogramming human fibroblasts" Cell Rep. (Year: 2017).*

(Continued)

*Primary Examiner* — Tracy Vivlemore
*Assistant Examiner* — John David Moore
(74) *Attorney, Agent, or Firm* — NORTON ROSE FULBRIGHT US LLP

(57) ABSTRACT

Embodiments of the disclosure include treatments of subconcussive and/or concussive brain damage by administering fibroblasts and/or fibroblasts cultured with one or more types of immunocytes. In one specific embodiment fibroblasts are cultured with monocytes in the presence of patient-specific T cells, and subsequently the T cells are re-administered into the patient. In one particular embodiment, products derived from fibroblast-immunocyte mixtures are comprised of cellular lysate, apoptotic bodies, exosomes, and/or other microvesicles. In one embodiment, the fibroblast cells and/or products derived from the fibroblast cells are administered subsequent to one or multiple head injuries. In other embodiments, products are administered in combination with neurorestorative and/or neuroprotective interventions.

30 Claims, 10 Drawing Sheets

(56) References Cited

FOREIGN PATENT DOCUMENTS

| WO | WO-2010071862 A1 | 6/2010 |
|----|------------------|--------|
| WO | WO-2011015862 A1 | 2/2011 |
| WO | WO 2012/004566 | 1/2012 |
| WO | WO-2013070880 A1 | 5/2013 |
| WO | WO-2014026012 A2 | 2/2014 |
| WO | WO-2015035395 A1 | 3/2015 |
| WO | WO 2016/161290 | 10/2016 |
| WO | WO-2017023689 A1 | 2/2017 |
| WO | WO 2018/013612 | 1/2018 |
| WO | WO 2018/015945 | 1/2018 |
| WO | WO-2018083700 A1 | 5/2018 |
| WO | WO 2018/132594 | 7/2018 |
| WO | WO-2018195308 A1 | 10/2018 |
| WO | WO-2019094617 A1 | 5/2019 |
| WO | WO-2019108756 A1 | 6/2019 |
| WO | WO-2019191830 A1 | 10/2019 |
| WO | WO-2019213518 A1 | 11/2019 |
| WO | WO-2020093050 A2 | 5/2020 |
| WO | WO-2020093051 A1 | 5/2020 |
| WO | WO 2020/146874 | 7/2020 |
| WO | WO-2020144380 A1 | 7/2020 |
| WO | WO 2021/050583 | 3/2021 |
| WO | WO-2021097423 A1 | 5/2021 |
| WO | WO-2021134081 A1 | 7/2021 |
| WO | WO-2021178395 A1 | 9/2021 |
| WO | WO-2021211386 A1 | 10/2021 |
| WO | WO-2021216460 A1 | 10/2021 |
| WO | WO-2021232064 A2 | 11/2021 |
| WO | WO-2022047486 A2 | 3/2022 |

OTHER PUBLICATIONS

Rossi et al., "Hematopoietic stem cell characterization and isolation" Methods Mol Biol. (Year: 2013).*

Shengying Li et al., "characteristics of human umbilical cord mesenchymal stem cells during ex vivo expansion" Molecular Medicine Reports (Year: 2015).*

Weston et al., "The potential of stem cells in treatment of traumatic brain injury" Curr Neurol Neuro Sci Rep (Year: 2018).*

American College of Surgeons "Best Practices Guidelines: The management of traumatic brain injury" (Year: 2024).*

DVSStem "Stem cell therapy for TBI: mechanisms and effectiveness" (Year: 2025).*

Yoder, "Endothelial stem and progenitor cells" (Stem cells): (2017 Grover Conference Series) Pulm Circ (Year: 2017).*

Wang et al. "an update on diagnostic and prognostic biomarkers from traumatic brain injury" Expert Rev Mol Diagn (Year: 2019).*

Anderson et al., "Mesenchymal stem cell-based therapy for ischemic stroke," Chinese Neurosurgical Journal, 2(1): pp. 1-6, 2016.

Dekosky et al., "Interleukin-1 receptor antagonist suppresses neurotrophin response in injured rat brain," Annals of Neurology, Jan. 1996, vol. 39, No. 1.

Denu et al., "Fibroblasts and mesenchymal stromal/stem cells are phenotypically indistinguishable," 136(2):85-97, 2016.

English translation of Office Communication issued in Japanese Patent Application No. 2021-524164, dated Jul. 14, 2023.

Extended European Search Report issued in European Patent Application No. 19878521.4, dated Oct. 7, 2022.

Ichim et al., "Fibroblasts as a practical alternative to mesenchymal stem cells," Journal of Translational Medicine, 16(1): pp. 1-9, 2018.

Morita, "A subpopulation of fibroblasts Muse cells, ameliorate rat stroke model," J. Physiol. Sci., 65(Suppl. 1), p. s76(S41-1), 2015.

Oguma et al., "Single-cell RNA sequencing reveals different signatures of mesenchymal stromal cell pluripotent-like and multipotent populations," iScience, 25(11):105395, 25 pages, 2022.

Wernig et al., "Neurons derived from reprogrammed fibroblasts functionally integrate into the fetal brain and improve symptoms of rats with Parkinson's disease," Proceedings of the National Academy of Science, Apr. 15, 2008, vol. 105, No. 15, pp. 5856-5867.

Yamashita et al., "Non-Tumorigenic Pluripotent Reparative Muse Cells Provide a New Therapeutic Approach for Neurologic Diseases," Cells, 10:961, 21 pages, 2021.

International Search Report and Written Opinion issued in International Application No. PCT/US2020/049949, mailed Jan. 7, 2021.

Official Communication issued in Canadian Patent Application No. 3118760, mailed Dec. 13, 2024.

Uchida et al., "Transplantation of Unique Subpopulation of Fibroblasts, Muse Cells, Ameliorates Experimental Stroke Possibly via Robust Neuronal Differentiation", Stem Cells, 34(1):160-173, 14 pages, 2015.

Chou et al., "Intracerebral transplantation of erythropoietin-producing fibroblasts facilitates neurogenesis and functional recovery in an ischemic stroke model," Brain and Behavior, 9(5):e01274, 11 pages, 2019.

Extended European Search Report issued in European Patent Application No. 20862683.8, dated Sep. 27, 2023.

Huang et al., "Multilineage Differentiation Potential of Fibroblast-like Stromal Cells Derived from Human Skin," Tissue Engineering Part A, 16(5):1491-1501, 2010.

Balducci et al. "Chapter 30: The differences between mesenchymal stroma cells and fibroblasts" in: Atkinson, K. The Biology and Therapeutic Application of Mesenchymal Cells, John Wiley & Sons, Inc., 2017, pp. 441-455.

Chen et al., "Brain-Derived Neurotrophic Factor-Transfected and Nontransfected 3T3 Fibroblasts Enhance Migratory Neuroblasts and Functional Restoration in Mice With Intracerebral Hemorrhage", Neuropathol Exp. Neurol., 71(12):1123-1136, 14 pages, 2012.

Fries et al. "Evidence of Fibroblast Heterogeneity and the Role of Fibroblast Subpopulations in Fibrosis" Clinical Immunology and Immunopathology vol. 72, No. 3, Sep. 1994, pp. 283-292.

Lee et al. "Identification of a distinct subpopulation of fibroblasts from murine dermis: CD73(−) CD105(+) as potential marker of dermal fibroblasts subset with multipotency" Cell Biol Int. 40(9), Sep. 2016, (abstract only).

Li et al., "Conversion of astrocytes and fibroblasts into functional noradrenergic neurons", Cell Reports, 28:682-697, 2019.

Lim et al., "Therapeutic effects of human umbilical cord blood-derived mesenchymal stem cells after intrathecal administration by lumbar puncture in a rat model of cerebral ischemia", Stem Cell Research & Therapy, 2(38):1-13, 13 pages, 2011.

Morsing et al. "Evidence of two distinct functionally specialized fibroblast lineages in breast stroma" Breast Cancer Research 18:108, 2016, pp. 1-11.

Sun et al., "Intranasal delivery of hypoxia-preconditioned bone marrow-derived mesenchymal stem cells enhanced regenerative effects after intracerebral hemorrhagic stroke in mice", Experimental Neurology, 272:78-87, 10 pages, 2015.

Wang et al., "Roles of Chemokine CXCL12 and its Receptors in Ischemic Stroke", Current Drug Targets, 13:166-172, 7 pages, 2012.

Amitani H., et al., "Mechanism and Nutrition in Cachexia," Japanese Journal of Psychosomatic Medicine, 2016, vol. 56, No. 10, pp. 1013-1022, (English abstract on p. 1022.).

Arbelaez-Quintero I., et al., "To Use or Not to Use Metformin in Cerebral Ischemia: A Review of the Application of Metformin in Stroke Rodents," Stroke Research and Treatment, 2017, vol. 2017, 13 pages.

Balducci L., et al., "Chapter 30: The Differences Between Mesenchymal Stroma Cells and Fibroblasts," in: Atkinson K., The Biology and Therapeutic Application of Mesenchymal Cells, John Wiley & Sons, Inc., 2017, pp. 441-455.

Bhang Sh, et al., "Basic fibroblast growth factor promotes bone marrow stromal cell transplantation-mediated neural regeneration in traumatic brain injury," Biochemical and Biophysical Research Communications, 2007, vol. 359, No. 1, pp. 40-45.

Caplan H., et al., "Mesenchymal Stromal Cell Therapeutic Delivery: Translational Challenges to Clinical Application," Frontiers in Immunology, 2019, vol. 10, art. 1645, 15 pages.

Carson J.A., et al., "Interleukin-6 as a Key Regulator of Muscle Mass during Cachexia," Exercise and Sport Sciences Reviews, Oct. 2010, vol. 38, No. 4, pp. 168-176.

(56)　　　　References Cited

OTHER PUBLICATIONS

Cohen S.P., et al., "A Double-Blind, Placebo-Controlled, Dose-Response Pilot Study Evaluating Intradiscal Etanercept in Patients with Chronic Discogenic Low Back Pain or Lumbosacral Radiculopathy," Anesthesiology, Jul. 2007, vol. 107, No. 01, pp. 99-105.

Cosme et al. "Hypoxia-Induced Changes in the Fibroblast Secretome, Exosome, and Whole-Cell Proteome Using Cultured, Cardiac-Derived Cells Isolated from Neonatal Mice", Journal of Proteome Research. Aug. 4, 2017, Epub Jul. 6, 2017, vol. 16, No. 8; pp. 2836-2847.

Costa-Almeida R., et al., "Fibroblasts as Maestros Orchestrating Tissue Regeneration," Journal of Tissue Engineering and Regenerative Medicine, Jan. 1, 2018, vol. 12, No. 01, doi: 10.1002/term. 2405, pp. 240-251, Retrieved from the Internet: URL: https://api. wiley.com/onlinelibrary/tdm/v1/articles/10.1002%2Fterm.2405, XP055956264.

Cox CS, "Cellular therapy for traumatic neurological injury," Pediatric Research, vol. 83, No. 1, pp. 325-332 (Jan. 2018).

Cox J.R., et al., "Treatment of Severe Adult Traumatic Brain Injury Using Bone Marrow Mononuclear Cells," Stem Cells, Nov. 1, 2016, vol. 35, pp. 1065-1079.

Denu R. A. et al., "Fibroblasts and Mesenchymal Stromal/Stem Cells Are Phenotypically Indistinguishable," Acta Haematologica, Aug. 2016, vol. 136, No. 02, doi: 10.1159/000445096, pp. 85-97, Retrieved from the Internet: URL: https://www.karger.com/Article/Pdf/445096, XP055828076.

English Translation of Office Communication issued in Japanese Patent Application No. 2021- 524163, dated Jul. 26, 2023, 10 pages.

English translation of Office Communication issued in Japanese Patent Application No. 2021-525028, dated Sep. 5, 2023, 10 pages.

Extended European Search Report issued in European Application No. 22896789.9, mailed on Sep. 25, 2025, 07 pages.

Extended European Search Report issued in European Patent Application No. 19878537.0, dated Jun. 22, 2022, 09 pages.

Extended European Search Report issued in European Patent Application No. 19881814.8, dated Sep. 21, 2022, 09 pages.

Extended European Search Report issued in European Patent Application No. 20886462.9, dated Oct. 13, 2023, 9 pages.

Extended European Search Report issued in European Patent Application No. 24182563.7, dated Nov. 8, 2024, 8 pages.

Hematti P., "Mesenchymal Stromal Cells and Fibroblasts: A Case of Mistaken Identity," Cytotherapy, Mar. 29, 2012, vol. 14, pp. 516-521.

Hematti P., "Mesenchymal Stromal Cells and Fibroblasts: A Case of Mistaken Identity," Cytotherapy, May 2012, vol. 14, No. 05, pp. 516-521, doi: 10.3109/14653249.2012.677822.

Huangfu, D. et al. "Induction of Pluripotent Stem Cells from Primary Human Fibroblasts with Only Oct4 and Sox2," Nature Biotechnology, vol. 26, No. 11. Nov. 2008, pp. 12691275.

International Search Report and Written Opinion for Application No. PCT/US2021/070642, dated Aug. 16, 2021, 10 pages.

International Search Report and Written Opinion for Application No. PCT/US2021/071296, dated Feb. 15, 2022, 15 pages.

International Search Report and Written Opinion for International Application No. PCT/US2019/030596, mailed Jul. 12, 2019, 9 Pages.

International Search Report and Written Opinion for International Application No. PCT/US2019/059678, mailed Jan. 27, 2020, 10 Pages.

International Search Report and Written Opinion for International Application No. PCT/US2019/060397, mailed Feb. 18, 2020, 8 Pages.

International Search Report and Written Opinion for International Application No. PCT/US2020/060724, mailed Mar. 10, 2021, 9 Pages.

International Search Report and Written Opinion Issued in International Application No. PCT/US2019/059683, Mailed on Jan. 30, 2020, 16 pages.

Invitation to Pay Additional Fees issued in International Application No. PCT/US2021/071296, dated Dec. 2, 2021, 2 pages.

Jordana M. et al al., "Immune-Inflammatory Functions of Fibroblasts," European Respiratory Journal, Dec. 1, 1994, vol. 07, No. 12, doi:10.1183/09031936.94.07122212, ISSN 0903-1936, pp. 2212-2222.

Kaur J., et al., "Mental Imagery as a Rehabilitative Therapy for Neuropathic Pain in People With Spinal Cord Injury: A Randomized Controlled Trial," Neurorehabilitation and Neural Repair, vol. 34, No. 11, 2020, pp. 1038-1049.

Lefvre, S. et al., "Synovial Fibroblasts Spread Rheumatoid Arthritis to Unaffected Joints," Nature Medicine, vol. 15, No. 12, Dec. 2009, pp. 1414-1420.

Lin, W., et al., "Mesenchymal Stem Cells Homing to Improve Bone Healing," Journal of Orthopaedic Translation, vol. 9, 2017, pp. 1927.

Liu S., et al., "Mouse-induced Pluripotent Stem Cells Generated Under Hypoxic Conditions in the Absence of Viral Infection and Oncogenic Factors and Used for Ischemic Stroke Therapy," Stem Cells and Development, 2014, 23(4), pp. 421-433.

Liu X., et al., "The Immunogenicity and Immune Tolerance of Pluripotent Stem Cell Derivatives," Frontiers in Immunology, 2017, vol. 8, art. 645, 6 pages.

Loupy A., et al al., "Immune Response After Pig-to-human Kidney Xenotransplantation: a Multimodal Phenotyping Study," Lancet, 2023, vol. 402, pp. 1158-1169.

Maqbool A., et al., "The Substrate-binding protein in bacterial abc transporters: dissecting roles in the evolution of substrate specificity," Biochemical Society Transactions, 2015, vol. 43(5), pp. 10111017.

Mastri M., et al., "Enhancing the Efficacy of Mesenchymal Stem Cell Therapy," World Journal of Stem Cells, Apr. 26, 2014, vol. 06, No. 02, ISSN 0005144886, pp. 82-93.

Mcginnis A., et al., "Animal Models of Pain and Anti-inflammatory Treatments," in Neuroimmune Interactions in Pain, Springer Nature Switzerland AG, 2023, pp. 43-85.

Meazza C., et al., "Effect of Growth Hormone (GH) on the Immune System," Pediatric Endocrinology Reviews, Aug. 2004, vol. 01, No. 03, pp. 490-495.

Office Communication issued in Canadian Patent Application No. 3,119,259, dated Feb. 1, 2024, 6 pages.

PCT International Search Report and Written Opinion issued in International Application No. PCT/US2021/026752, dated Aug. 12, 2021, 11 Pages PCT International Search Report and Written Opinion issued in International Application No. PCT/US/2022/080206, dated Feb. 21, 2023, 12 pages.

Rana N.K., et al., "CoCI2 Simulated Hypoxia Induce Cell Proliferation and Alter the Expression Pattern of Hypoxia Associated Jenes Involved in Angiogenesis and Apoptosis," Biology Research, vol. 52, No. 1, Article 12, 2019, 13 pages.

Rosochowicz M. A., et al., "Conditioned Medium - Is It an Undervalued Lab Waste with the Potential for Osteoarthritis Management?," Stem Cell Reviews and Reports, 2023, vol. 19, pp. 1185-1213.

Sharma K. K., et al., "Neuropathy, Its Profile and Experimental Nerve Injury Neuropathic Pain Models: a Review," Current Pharmaceutical Design, 2023, vol. 29, pp. 3343-3356.

Sheng Z., et al., "Efficacy of Minocycline in Acute Ischemic Stroke: A Systemic Review and Meta-Analysis of Rodent and Clinical Studies," Frontiers in Neurology, 2018, 9(1103), 12 pages.

Shi, P. et al. "Therapeutic Effects of Cell Therapy with Neonatal Human Dermal Fibroblasts and Rabbit Dermal Fibroblasts on Disc Degeneration and Inflammation," The Spine Journal, vol. 18, 2018, p. 111.

Shinotsuka N., et al., "Fibroblasts: the Neglected Cell Type in Peripheral Sensitisation and Chronic Pain a Review Based on a Systematic Search of the Literature," BMJ Open Science. 2022;6:e100235. DOI: 10.1136/bmjos-2021-100235, 11 pages.

Stappenbeck T.S., et al., "The Role of Stromal Stem Cells in Tissue Regeneration and Wound Repair," Science, Jun. 26, 2009, vol. 324, No. 5935, doi: 10.1126/science. 1172687, ISSN 0036-8075, pp. 1666-1669, Retrieved from the Internet: URL: http://dx.doi.org/10. 1126/science.1172687.

(56)                References Cited

OTHER PUBLICATIONS

Sun D, et al., "Basic Fibroblast Growth Factor-enhanced Neurogenesis Contributes to Cognitive Recovery in Rats Following Traumatic Brain Injury," Experimental Neurology, Mar. 1, 2009, vol. 216, No. 1, pp. 56-65.

Sun X., et al., "CXCL12/CXCR4/CXCR7 Chemokine Axis and Cancer Progression," Cancer and Metastasis Reviews, Dec. 2010, vol. 29, No. 04, pp. 709-722.

Tang C, et al., "FGF2 Attenuates Neural Cell Death via Suppressing Autophagy After Rat Mild Traumatic Brain Injury," Stem Cells International, 2017, vol. 2017, Article ID 2923182, 11 pages.

Tassew N.G., et al., "Exosomes Mediate Mobilization of Autocrine Wnt10b to Promote Axonal Regeneration in the Injured CNS," Cell Reports, 2017, 20(1), pp. 99-111.

Teicher B.A., et al., "CXCL12 (SDF-1)/CXCR4 Pathway in Cancer," Clinical Cancer Research, Molecular Pathways, Jun. 1, 2010, vol. 16, No. 11, pp. 2927-2931.

Thau-Zuchman O, et al., "Combination of Vascular Endothelial and Fibroblast Growth Factor 2 for Induction of Neurogenesis and Angiogenesis After Traumatic Brain Injury," May 2012), Journal of Molecular Neuroscience, vol. 47, No. 1, pp. 166-172.

Vadala G., et al., "Stem Cells Sources for Intervertebral Disc Regeneration," World Journal of Stem Cells, May 26, 2016, vol. 08, No. 05, pp. 185-201.

Wang X., et al., "Hypoxia Precondition Promotes Adipose-Derived Mesenchymal Stem Cells Based Repair of Diabetic Erectile Dysfunction via Augmenting Angiogenesis and Neuroprotection," PLoS One, vol. 10, No. 3, Article e0118951, 2015, 18 pages.

Wikipedia, "Muscle," Wikipedia.com, Mar. 30, 2018, 2 pages.

Wong T., et al., "The Role of Fibroblasts in Tissue Engineering and Regeneration," British Journal of Dermatology, Jun. 1, 2007, vol. 156, No. 06, pp. 1149-1155.

Zeddou M., et al., "Umbilical Cord Fibroblasts: Could They Be Considered As Mesenchymal Stem Cells?," World J Stem Cells (World Journal of Stem Cells, 2014, vol. 6, No. 3, pp. 367-370.

Zhao B., et al., "Hypoxia drives the transition of human dermal fibroblasts to a myofibroblast-like phenotype via the TGF-b1/Smad3 pathway," International Journal of Molecular Medicine, vol. 39, 2017, pp. 153-159.

* cited by examiner

Fibroblasts Synergize with Monocytes at Producing BDNF

Fibroblasts Synergize with CD34 Hematopoietic Cells at Producing BDNF

Fibroblasts Synergize with Bone Marrow MSC at Producing BDNF

Fibroblasts Synergize with Monocytes to Inhibit Neuron Death

Fibroblasts Synergize with CD34 Hematopoietic Cells to Inhibit Neuron Death

Fibroblasts Synergize with MSC to Inhibit Neuron Death

Fibroblasts Synergize with CD34 to Stimulate Neurogenesis

Fibroblasts Synergize with MSC to Stimulate Neurogenesis

FIG. 9

FIBROBLAST AND FIBROBLAST-IMMUNOCYTE COMBINATIONS FOR TREATMENT OF SUBCONCUSSIVE- AND CONCUSSIVE-ASSOCIATED NEUROLOGICAL DAMAGE

This application is a national phase application under 35 U.S.C. § 371 that claims priority to International Application No. PCT/US2020/049949, filed Sep. 9, 2020, which claims priority to U.S. Provisional Patent Application Ser. No. 62/897,428, filed Sep. 9, 2019, which isboth of which are incorporated by reference herein in their entirety.

TECHNICAL FIELD

Embodiments of the disclosure encompass at least the fields of cell biology, molecular biology, neurology, physiology, biochemistry, immunology, and medicine.

BACKGROUND

Chronic Traumatic Encephalopathy (CTE) has been originally described in the sport of boxing under the name "punch drunk syndrome". It is known that professional boxers with multiple bouts and repeated head blows are prone to chronic traumatic encephalopathy (CTE). Repeated head blows produce rotational acceleration of the brain, diffuse axonal injury, and other neuropathological features. CTE includes motor changes such as tremor, dysarthria, and parkinsonism; cognitive changes such as mental slowing and memory deficits; and psychiatric changes such as explosive behavior, morbid jealousy, pathological intoxication, and [1-6].

It is believed that in England at least 17% of boxers have CTE disturbed gait and coordination, slurred speech and tremors, as well as cerebral dysfunction causing cognitive impairments and neurobehavioural disturbances [7]. In one study, diffusion tensor imaging (DTI), which is sensitive to microscopic white matter changes when routine MR imaging is unrevealing [8, 9], was used together with tract-based spatial statistics (TB SS) together with neuropsychological examination of executive functions and memory to investigate a collective of 31 male amateur boxers and 31 age-matched controls as well as a subgroup of 19 individuals, respectively, who were additionally matched for intellectual performance (IQ). It was found that participants had normal findings in neurological examination and conventional MR. Amateur boxers did not show deficits in neuropsychological tests when their IQ was taken into account. Fractional anisotropy was significantly reduced, while diffusivity measures were increased along central white matter tracts in the boxers group. These changes were in part associated with the number of fights. This study demonstrated that TBSS revealed widespread white matter disturbance partially related to the individual fighting history in amateur boxers. These findings closely resemble those in patients with accidental TBI and indicate similar histological changes in amateur boxers [10].

In addition to boxing, Jockeys have also been reported to suffer from CTE, in a 1976 publication, Foster et al reported Five National Hunt jockeys have been found to have post-traumatic encephalopathy—three with epilepsy and two with significant intellectual and psychological deterioration [11]. Other reports of jockey's having similar situations have been described [12]. Numerous other causes of CTE have been described including whiplash [13], shaken baby syndrome [14], wrestling [15], military combat [16, 17], football [18-22], rugby [23], soccer [24, 25], jail head trauma [26], shotgun injury [27], mixed martial arts [28], One study in the journal JAMA examined a case series of 202 football players whose brains were donated for research. Neuropathological evaluations and retrospective telephone clinical assessments (including head trauma history) with informants were performed blinded. Online questionnaires ascertained athletic and military history. Neuropathological diagnoses of neurodegenerative diseases, including CTE, based on defined diagnostic criteria; CTE neuropathological severity (stages I to IV or dichotomized into mild [stages I and II] and severe [stages III and IV]); informant-reported athletic history and, for players who died in 2014 or later, clinical presentation, including behavior, mood, and cognitive symptoms and dementia. Among 202 deceased former football players (median age at death, 66 years [interquartile range, 47-76 years]), CTE was neuropathologically diagnosed in 177 players (87%; median age at death, 67 years [interquartile range, 52-77 years]; mean years of football participation, 15.1 [SD, 5.2]), including 0 of 2 pre-high school, 3 of 14 high school (21%), 48 of 53 college (91%), 9 of 14 semiprofessional (64%), 7 of 8 Canadian Football League (88%), and 110 of 111 National Football League (99%) players. Neuropathological severity of CTE was distributed across the highest level of play, with all 3 former high school players having mild pathology and the majority of former college (27 [56%]), semiprofessional (5 [56%]), and professional (101 [86%]) players having severe pathology. Among 27 participants with mild CTE pathology, 26 (96%) had behavioral or mood symptoms or both, 23 (85%) had cognitive symptoms, and 9 (33%) had signs of dementia. Among 84 participants with severe CTE pathology, 75 (89%) had behavioral or mood symptoms or both, 80 (95%) had cognitive symptoms, and 71 (85%) had signs of dementia. In a convenience sample of deceased football players who donated their brains for research, a high proportion had neuropathological evidence of CTE, suggesting that CTE may be related to prior participation in football [29].

In another study the authors examined the effect of age of first exposure to tackle football on chronic traumatic encephalopathy (CTE) pathological severity and age of neurobehavioral symptom onset in tackle football players with neuropathologically confirmed CTE. The sample included 246 tackle football players who donated their brains for neuropathological examination. Two hundred eleven were diagnosed with CTE (126 of 211 were without comorbid neurodegenerative diseases), and 35 were without CTE. Informant interviews ascertained age of first exposure and age of cognitive and behavioral/mood symptom onset. Analyses accounted for decade and duration of play. Age of exposure was not associated with CTE pathological severity, or Alzheimer's disease or Lewy body pathology. In the 211 participants with CTE, every 1 year younger participants began to play tackle football predicted earlier reported cognitive symptom onset by 2.44 years (p<0.0001) and behavioral/mood symptoms by 2.50 years (p<0.0001). Age of exposure before 12 predicted earlier cognitive (p<0.0001) and behavioral/mood (p<0.0001) symptom onset by 13.39 and 13.28 years, respectively. In participants with dementia, younger age of exposure corresponded to earlier functional impairment onset. Similar effects were observed in the 126 CTE-only participants. Effect sizes were comparable in participants without CTE. In this sample of deceased tackle football players, younger age of exposure to tackle football was not associated with CTE pathological severity, but predicted earlier neurobehavioral symptom onset. Youth exposure to tackle football may reduce resiliency to late-life neuropathology [30].

The present disclosure provides effective treatment or prevention of CTE and other types of subconcussive-associated and concussive-associated neurological damage.

BRIEF SUMMARY

The disclosure pertains to the area of head trauma, and more particularly the disclosure pertains to the field of chronic traumatic encephalopathy (CTE), including the field of regenerative medicine for treatment of CTE.

Disclosed are new, useful and non-obvious methodologies and compositions of matter for the treatment of subconcussive and/or concussive brain damage resulting in pathologies such as altered condition and chronic traumatic encephalopathy (CTE) using fibroblasts and/or fibroblasts cultured with immunocytes of any kind and/or stem cells of any kind. In one embodiment of the disclosure, the cellular combinations are administered to: a) reduce oxidative stress; b) suppress inflammation; c) enhance neurogenesis; and/or d) stimulate axonal regrowth. In one embodiment, fibroblasts (such as derived from umbilical cord and/or other perinatal tissues (for example)) are cultured with immune cells (such as monocytes) in the presence of patient-specific T cells, and subsequently the T cells are re-administered into the patient. In another embodiment, the fibroblasts are bone marrow-derived. In yet another embodiment the fibroblast cells are adipose-derived. In one embodiment, products derived from fibroblast-immunocyte mixtures are comprised of cellular lysate, apoptotic bodies, exosomes, and other microvesicles. In one embodiment, the fibroblast cells and/or products derived from the fibroblast cells are administered subsequent to one or more head injuries of any kind. In other embodiments, the products are administered with neuro-restorative and/or neuroprotective interventions, whether or not at the same time as administration of any cells.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawings.

FIG. 9 demonstrates that fibroblasts synergize with MSCs to stimulate neurogenesis. The bars from left to right are control, fibroblasts alone, MSCs alone, and a mixture of fibroblasts and MSCs.

DETAILED DESCRIPTION

I. Definitions

Figure 1:
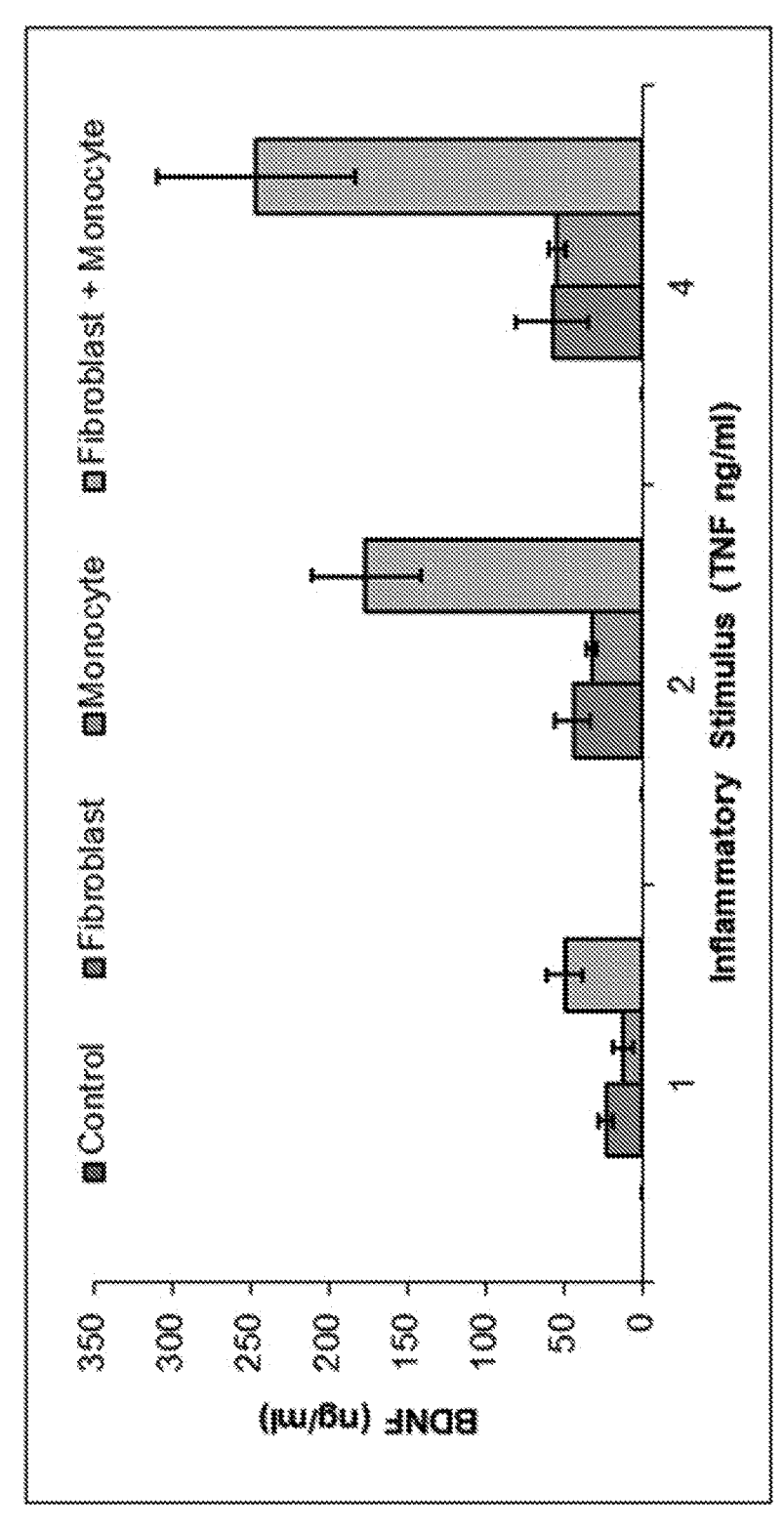
FIG. 1 shows that fibroblasts synergize with monocytes at producing Brain-derived neurotrophic factor (BDNF). The bars from left to right are control, fibroblasts alone, monocytes alone, and a mixture of fibroblasts and monocytes.

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%. With respect to biological systems or processes, the term can mean within an order of magnitude, such as within 5-fold, and such as within 2-fold, of a value. Unless otherwise stated, the term 'about' means within an acceptable error range for the particular value.

The term "administered" or "administering", as used herein, refers to any method of providing a composition to an individual such that the composition has its intended effect on the individual. For example, one method of administering is by an indirect mechanism using a medical device such as, but not limited to a catheter, applicator gun, syringe, etc. A second exemplary method of administering is by a direct mechanism such as, local tissue administration, oral ingestion, transdermal patch, topical, inhalation, suppository, etc.

As used herein, "allogeneic" refers to tissues or cells or other material from another body that in a natural setting are immunologically incompatible or capable of being immunologically incompatible, although from one or more individuals of the same species.

As used herein, the term "allotransplantation" refers to the transplantation of organs, tissues, and/or cells from a donor to a recipient, where the donor and recipient are different individuals, but of the same species. Tissue transplanted by such procedures is referred to as an allograft or allotransplant.

As used herein, the terms "allostimulatory" and "alloreactive" refer to stimulation and reaction of the immune system in response to an allologous antigens, or "alloantigens" or cells expressing a dissimilar HLA haplotype.

As used herein, "autologous" refers to tissues or cells or other material that are derived or transferred from the same individual's body (i.e., autologous blood donation; an autologous bone marrow transplant).

As used herein, the term "autotransplantation" refers to the transplantation of organs, tissues, and/or cells from one part of the body in an individual to another part in the same individual, i.e., the donor and recipient are the same individual. Tissue transplanted by such "autologous" procedures is referred to as an autograft or autotransplant.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells that lack protein activity with an expression vector that expresses the protein, a derivative thereof, or a portion thereof. In other cases, a fragment of a gene product (such as a protein) may be considered biologically active (or it may be referred to as functionally active) if it retains the activity of the full-length gene product, although it may be at a reduced but detectable level of the activity of the full-length gene product.

"Cell culture" is an artificial in vitro system containing viable cells, whether quiescent, senescent or (actively) dividing. In a cell culture, cells are grown and maintained at an appropriate temperature, such as a temperature of 37° C. and under an atmosphere typically containing oxygen and $CO_2$, although in other cases these are altered. Culture conditions may vary widely for each cell type though, and variation of conditions for a particular cell type can result in different phenotypes being expressed. The most commonly varied factor in culture systems is the growth medium. Growth media can vary in concentration of nutrients, growth factors, and the presence of other components. The growth factors used to supplement media are often derived from animal blood, such as calf serum.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The term "drug", "agent" or "compound" as used herein, refers to any pharmacologically active substance capable of being administered that achieves a desired effect. Drugs or compounds can be synthetic or naturally occurring, nonpeptide, proteins or peptides, oligonucleotides, or nucleotides (DNA and/or RNA), polysaccharides or sugars.

The term "individual", as used herein, refers to a human or animal that may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants. It is not intended that the term "individual" connote a need for medical treatment, therefore, an individual may voluntarily or involuntarily be part of experimentation whether clinical or in support of basic science studies. The term "subject" or "individual" refers to any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

II. Embodiments

The disclosure encompasses the treatment and prevention of medical conditions associated with the brain, including from injury and/or disease. Certain methods of the disclosure treat or prevent neurological damage. The medical condition may be a neurological disorder. Any kind of brain injury may be treated or prevented, including traumatic brain injury. The injury may comprise hematoma, hemorrhage, concussion, edema, a mixture thereof, and so forth. Types of traumatic brain injuries include brain contusion, second impact syndrome, Coup-Contrecoup brain injury, shaken baby syndrome, and/or penetrating injury.

The medical conditions may be the result of a single injury or repeated injuries, in some cases. The injuries may be from physical contact, including as the result of a vocation and/or sport. Any injuries may have occurred at any time during the life of the individual, including years, months, days, or weeks prior to the onset of any one or more symptoms. In particular embodiments, the medical condition is chronic traumatic encephalopathy (CTE), including dementia pugilistica. The individual may be an athlete, including one that is involved recreationally or professionally in football, boxing, wrestling, soccer, hockey, lacrosse, basketball, baseball, softball, rugby, and so forth. The athlete may be at risk for injury because of the sport and in need of prevention. The individual may have a medical condition such as a head injury related to their job, such as a construction worker, first responder, warehouse worker, and so forth. The worker of any kind may be at risk for injury because of their vocation and in need of prevention.

In particular embodiments, the disclosure encompasses the novel, useful, and unexpected finding that administration of fibroblasts and fibroblasts with other cells, such as mesenchymal stem cells, monocytes and/or hematopoietic stem cells, for example, causes a series of biochemical and cellular reactions that permits enhanced production of one or more regenerative factors and are useful for the regeneration/protection/prophylaxis in individuals suffering from concussive and/or subconcussive injuries, which in some cases are associated with development of CTE. More specifically, the disclosure provides means of using fibroblasts cells, and/or combination of fibroblast cells with one or more other compositions (including cells) to inhibit the progressive neuronal loss, cognitive loss, and microglial activation as a result of CTE. In one embodiment the disclosure, there is administration of an effective amount of fibroblast cells as a means of enhancing the function of neurons and/or protecting neurons in an individual with CTE.

In some embodiments, fibroblasts are utilized in an autologous manner for an individual. In another embodiment, allogeneic fibroblasts are utilized for the practice of the methods of the disclosure. Various sources of fibroblasts may be used for the practice of the methods of the disclosure, and these include: a) foreskin; b) adipose tissue; c) skin biopsy; d) bone marrow; e) placenta; f) umbilical cord; g)

amneotic fluid; h) umbilical cord blood; i) ear lobe skin; j) embryonic fibroblasts; k) plastic surgery related by-product; and/or l) nail matrix.

In one embodiment, the disclosure encompasses the use of activation of fibroblasts prior to therapeutic use, and/or administration of one or more agents that act as "regenerative adjuvants" for the fibroblasts. In particular embodiments, the cells in the formulation display typical fibroblast morphologies when growing in cultured monolayers. Specifically, cells may display an elongated, fusiform or spindle appearance with slender extensions, or cells may appear as larger, flattened stellate cells that may have cytoplasmic leading edges. A mixture of these morphologies may also be observed. The cells may express proteins characteristic of normal fibroblasts including the fibroblast-specific marker, CD90 (Thy-1), a 35 kDa cell-surface glycoprotein, and the extracellular matrix protein, collagen, as examples. The fibroblast dosage formulation is an autologous cell therapy product comprised of a suspension of autologous fibroblasts, grown from a biopsy of each individual's own skin using standard tissue culture procedures. In one embodiment, the fibroblasts of the disclosure can also be used to generate other cell types for tissue repair and/or regeneration.

Embodiments of the disclosure include methods for treatment or prevention of subconcussive and/or concussive brain damage by administering to an individual in need thereof fibroblasts and/or fibroblasts cultured with one or more types of immunocytes. In one specific embodiment, fibroblasts are cultured with monocytes in the presence of T cells (autologous or allogeneic or xenogeneic with respect to the recipient individual), and subsequently the T cells are administered to the individual. In a particular embodiment, products derived from fibroblast-immunocyte mixtures are comprised of cellular lysate, apoptotic bodies, exosomes, and/or other microvesicles. In one embodiment, the fibroblast cells and/or products derived from the fibroblast cells are administered subsequent to one or multiple head injuries. In other embodiments, products are administered in combination with neurorestorative and/or neuroprotective interventions.

Embodiments of the disclosure include methods of treating or preventing a sub-concussive or concussive brain injury in an individual, comprising the steps of administering a therapeutically effective amount of regenerative cells and/or one or more products derived from regenerative cells; and if needed, repeating administration of said regenerative cells and/or products derived from said cells. The regenerative cells may be fibroblasts that have been cultured with one or more types of immunocytes and/or one or more types of stem cells. In specific cases, the fibroblasts have been cultured with monocytes, mesenchymal stem cells, and/or hematopoietic stem cells, and in some cases products from the fibroblasts at any step of the method are provided to an individual in need thereof. In some cases, the individual is identified as having one or more elevated inflammatory markers subsequent to a head and/or neck injury.

In embodiments wherein fibroblasts and/or products derived therefrom are delivered to an individual in need thereof, the fibroblasts may be naturally regenerative or may be manipulated to be regenerative. In such cases, the fibroblasts may express one or more specific markers and/or lack one or more specific markers. For example, the fibroblast cells may express a marker selected from the group consisting of Oct-4, Nanog, Sox-2, KLF4, c-Myc, Rex-1, GDF-3, LIF receptor, CD105, CD117, CD344 Stella, and a combination thereof. The fibroblast cells may additionally or alternatively express a marker selected from the group consisting of CD10, CD13, CD44, CD73, CD90, CD141, PDGFr-alpha, HLA-A, HLA-B, HLA-C, and a combination thereof. The fibroblast cells may additionally or alternatively may lack expression of a marker selected from the group consisting of MHC class I, MHC class II, CD45, CD13, CD49c, CD66b, CD73, CD105, CD90, and a combination thereof. The fibroblast cells may additionally or alternatively may lack expression of a marker selected from the group consisting of CD31, CD34, CD45, CD117, CD141, HLA-DR, HLA-DP, HLA-DQ, and a combination thereof.

In particular embodiments, any cells used in any methods encompassed herein are regenerative cells, and such cells may include a combination of fibroblasts with hematopoietic stem cells (and/or mesenchymal stem cells), optionally, immunocytes of any kind. The hematopoietic stem cells may be capable of multi-lineage reconstitution in an immunodeficient host. The hematopoietic stem cells may express the c-kit protein, the Sca-1 protein, CD34, and/or CD133, and they may lack expression of one or more lineage markers; they may lack expression of CD38; they may be positive for expression of c-kit and Sca-1 and substantially lack expression of one or more lineage markers.

In cases wherein mesenchymal stem cells are utilized, they may express one or more markers and they may lack expression of one or more markers. In a specific case, they express a marker selected from the group consisting of: a) CD73; b) CD90; c) CD105; and d) a combination thereof; and/or they may lack expression of a marker selected from the group consisting of: a) CD14; b) CD45; c) CD34; and d) a combination thereof.

In certain embodiments, mesenchymal stem cells are derived from specific tissues and as a result may express one or more markers and they may lack expression of one or more markers. In specific cases, they may be from tissues selected from the group consisting of: a) bone marrow; b) peripheral blood; c) adipose tissue; d) mobilized peripheral blood; e) umbilical cord blood; f) Wharton's jelly; g) umbilical cord tissue; h) skeletal muscle tissue; i) subepithelial umbilical cord; j) endometrial tissue; k) menstrual blood; l) fallopian tube tissue; and m) a combination thereof.

The fibroblasts utilized in the disclosure are generated, in one embodiment, by outgrowth from a biopsy of the recipient's own tissue (such as skin) (in the case of autologous preparations), or tissue (such as skin) of healthy donors (for allogeneic preparations). In some embodiments fibroblasts are used from young donors. In another embodiment fibroblasts are transfected with one or more genes to allow for enhanced growth and overcoming of the Hayflick limit. Subsequent to derivation of cells, there may be expansion in culture using standard cell culture techniques. Skin tissue (dermis and epidermis layers), for example, may be biopsied from a subject's post-auricular area. In one embodiment, the starting material is composed of three 3-mm punch skin biopsies collected using standard aseptic practices. The biopsies are collected by the treating physician, placed into a vial containing sterile phosphate buffered saline (PBS). The biopsies are shipped in a 2-8° C. refrigerated shipper back to the manufacturing facility. In one embodiment, after arrival at the manufacturing facility, the biopsy is inspected and, upon acceptance, transferred directly to the manufacturing area. Upon initiation of the process, the biopsy tissue is then washed prior to enzymatic digestion. After washing, a Liberase Digestive Enzyme Solution is added without mincing, and the biopsy tissue is incubated at 37.0±2° C. for one hour. Time of biopsy tissue digestion is a critical process parameter that can affect the viability and growth rate of cells in culture. Liberase is a collagenase/neutral protease enzyme cocktail obtained formulated from Lonza Walkersville, Inc. (Walkersville, Md.) and unformulated from Roche Diagnostics Corp. (Indianapolis, Ind.). Alternatively, other commercially available collagenases may be used, such as Serva Collagenase NB6 (Helidelburg, Germany). After digestion, Initiation Growth Media (IMDM, GA, 10% Fetal Bovine Serum (FBS)) is added to neutralize the enzyme, cells are pelleted by centrifugation and resuspended in 5.0 mL Initiation Growth Media. Alternatively, centrifugation is not performed, with full inactivation of the enzyme occurring by the addition of Initiation Growth Media only. Initiation Growth Media is added prior to seeding of the cell suspension into a T-175 cell culture flask for initiation of cell growth and expansion. A T-75, T-150, T-185 or T-225 flask can be used in place of the T-75 flask. Cells are incubated at 37±2.0° C. with 5.0±1.0% $CO_2$ and fed with fresh Complete Growth Media every three to five days. All feeds in the process are performed by removing half of the Complete Growth Media and replacing the same volume with fresh media. Alternatively, full feeds can be performed. Cells should not remain in the T-175 flask greater than 30 days prior to passaging. Confluence is monitored throughout the process to ensure adequate seeding densities during culture splitting. When cell confluence is greater than or equal to 40% in the T-175 flask, they are passaged by removing the spent media, washing the cells, and treating with Trypsin-EDTA to release adherent cells in the flask into the solution. Cells are then trypsinized and seeded into a T-500 flask for continued cell expansion. Alternately, one or two T-300 flasks, One Layer Cell Stack (1 CS), One Layer Cell Factory (1 CF) or a Two Layer Cell Stack (2 CS) can be used in place of the T-500 Flask. Morphology is evaluated at each passage and prior to harvest to monitor the culture purity throughout the culture purity throughout the process. Morphology is evaluated by comparing the observed sample with visual standards for morphology examination of cell cultures. The cells display typical fibroblast morphologies when growing in cultured monolayers. Cells may display either an elongated, fusiform or spindle appearance with slender extensions, or appear as larger, flattened stellate cells which may have cytoplasmic leading edges. A mixture of these morphologies may also be observed. Fibroblasts in less confluent areas can be similarly shaped, but randomly oriented. The presence of keratinocytes in cell cultures is also evaluated. Keratinocytes appear round and irregularly shaped and, at higher confluence, they appear organized in a cobblestone formation. At lower confluence, keratinocytes are observable in small colonies. Cells are incubated at 37±2.0° C. with 5.0±1.0% $CO_2$ and passaged every three to five days in the T-500 flask and every five to seven days in the ten layer cell stack (10CS). Cells should not remain in the T-500 flask for more than 10 days prior to passaging. Quality Control (QC) release testing for safety of the Bulk Drug Substance includes sterility and endotoxin testing. When cell confluence in the T-500 flask is about 95%, cells are passaged to a 10 CS culture vessel. Alternately, two Five Layer Cell Stacks (5 CS) or a 10 Layer Cell Factory (10 CF) can be used in place of the 10 CS. 10CS. Passage to the 10 CS is performed by removing the spent media, washing the cells, and treating with Trypsin-EDTA to release adherent cells in the flask into the solution. Cells are then transferred to the 10 CS. Additional Complete Growth Media is added to neutralize the trypsin and the cells from the T-500 flask are pipetted into a 2 L bottle containing fresh Complete Growth Media. The contents of the 2 L bottle are transferred into the 10 CS and seeded across all layers. Cells are then incubated at 37±2.0° C. with 5.0±1.0% $CO_2$ and fed with fresh Complete Growth Media every five to seven days. Cells should not remain in the 10CS for more than 20 days prior to passaging. In one embodiment, the passaged dermal fibroblasts are rendered substantially free of immunogenic proteins present in the culture medium by incubating the expanded fibroblasts for a period of time in protein free medium, Primary Harvest When cell confluence in the 10 CS is 95% or more, cells are harvested. Harvesting is performed by removing the spent media, washing the cells, treating with Trypsin-EDTA to release adherent cells into the solution, and adding additional Complete Growth Media to neutralize the trypsin. Cells are collected by centrifugation, resuspended, and in-process QC testing performed to determine total viable cell count and cell viability.

In a particular embodiment, about 50 million to 500 million fibroblast cells are administered to the subject. For example, about 50 million to about 100 million fibroblast cells, about 50 million to about 200 million fibroblast cells, about 50 million to about 300 million fibroblast cells, about 50 million to about 400 million fibroblast cells, about 100 million to about 200 million fibroblast cells, about 100 million to about 300 million fibroblast cells, about 100 million to about 400 million fibroblast cells, about 100 million to about 500 million fibroblast cells, about 200 million to about 300 million fibroblast cells, about 200 million to about 400 million fibroblast cells, about 200 million to about 500 million fibroblast cells, about 300 million to about 400 million fibroblast cells, about 300 million to about 500 million fibroblast cells, about 400 million to about 500 million fibroblast cells, about 50 million fibroblast cells, about 100 million fibroblast cells, about 150 million fibroblast cells, about 200 million fibroblast cells, about 250 million fibroblast cells, about 300 million fibroblast cells, about 350 million fibroblast cells, about 400 million fibroblast cells, about 450 million fibroblast cells or about 500 million fibroblast cells may be administered to the subject.

In some embodiments, fibroblast exosomes are used to decrease IL-17 production from cells of any kind. Exosomes for use in the current disclosure may be purified as follows: In one embodiment, fibroblasts are cultured using means known in the art for preserving viability and proliferative ability of fibroblasts. The disclosure may be applied both for individualized autologous exosome preparations and for exosome preparations obtained from established cell lines, for experimental or biological use. In one embodiment, this disclosure is more specifically based on the use of chromatography separation methods for preparing membrane vesicles, particularly to separate the membrane vesicles from potential biological contaminants, wherein said microvesicles are exosomes, and cells utilized for generating said exosomes are fibroblast cells.

For the practice of the disclosure, a particular embodiment is the administration of fibroblast cells alone or in combination with mesenchymal stem cells (MSC) intravenously at concentrations sufficient to prevent CTE and or reverse CTE.

"Mesenchymal stem cell" or "MSC" in some embodiments refers to cells that are (1) adherent to plastic, (2) express CD73, CD90, and CD105 antigens, while being CD14, CD34, CD45, and HLA-DR negative, and (3) possess ability to differentiate to osteogenic, chondrogenic and adipogenic lineage. Other cells possessing mesenchymal-like properties are included within the definition of "mesenchymal stem cell", with the condition that said cells possess at least one of the following: a) regenerative activity; b) production of growth factors; c) ability to induce a healing response, either directly, or through elicitation of endogenous host repair mechanisms. As used herein, "mesenchymal stromal cell" or mesenchymal stem cell can be used interchangeably.

MSC can be derived from any tissue including, but not limited to, bone marrow, adipose tissue, amniotic fluid, endometrium, trophoblast-derived tissues, cord blood, Wharton jelly, placenta, amniotic tissue, derived from pluripotent stem cells, and/or tooth. In some definitions of "MSC", the cells include cells that are CD34-positive upon initial isolation from tissue but are similar to cells described about phenotypically and functionally. As used herein, "MSC" may include cells that are isolated from tissues using cell surface markers selected from the list consisting of NGF-R, PDGF-R, EGF-R, IGF-R, CD29, CD49a, CD56, CD63, CD73, CD105, CD106, CD140b, CD146, CD271, MSCA-1, SSEA4, STRO-1 and STRO-3 and any combination thereof, and satisfy the ISCT criteria either before or after expansion. Furthermore, as used herein, in some contexts, "MSC" includes cells described in the literature as bone marrow stromal stem cells (BMSSC), marrow-isolated adult multipotent inducible cells (MIAMI) cells, multipotent adult progenitor cells (MAPC), mesenchymal adult stem cells (MASCS), MultiStem®, Prochymal®, remestemcel-L, Mesenchymal Precursor Cells (MPCs), Dental Pulp Stem Cells (DPSCs), PLX cells, PLX-PAD, AlloStem®, Astrostem®, Ixmyelocel-T, MSC-NTF, NurOwn™, Stemedyne™-MSC, Stempeucel®, StempeucelCLI, StempeucelOA, HiQCell, Hearticellgram-AMI, Revascor®, Cardiorel®, Cartistem®, Pneumostem®, Promostem®, Homeo-GH, AC607, PDA001, SB623, CX601, AC607, Endometrial Regenerative Cells (ERC), adipose-derived stem and regenerative cells (ADRCs).

MSC may be expanded and utilized by administration themselves, or may be cultured in a growth media in order to obtain conditioned media, the term Growth Medium generally refers to a medium sufficient for the culturing of umbilicus-derived cells. In particular, one particular medium for the culturing of the cells of the invention herein comprises Dulbecco's Modified Essential Media (also abbreviated DMEM herein). Particularly preferred is DMEM-low glucose (also DMEM-LG herein) (Invitrogen, Carlsbad, Calif.). The DMEM-low glucose is preferably supplemented with 15% (v/v) fetal bovine serum (e.g. defined fetal bovine serum, Hyclone, Logan Utah), antibiotics/antimycotics (preferably penicillin (100 Units/milliliter), streptomycin (100 milligrams/milliliter), and amphotericin B (0.25 micrograms/milliliter), (Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to Growth Medium.

Also relating to the present disclosure, the term standard growth conditions, as used herein may refer to culturing of cells at 37° C., in a standard atmosphere comprising 5% $CO_2$. Relative humidity is maintained at about 100%. While foregoing the conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like.

Mesenchymal stem cells ("MSC") were originally derived from the embryonal mesoderm and subsequently have been isolated from adult bone marrow and other adult tissues. They can be differentiated to form muscle, bone, cartilage, fat, marrow stroma, and/or tendon, in some cases.

Mesoderm also differentiates into visceral mesoderm that can give rise to cardiac muscle, smooth muscle, or blood islands consisting of endothelium and hematopoietic progenitor cells. The differentiation potential of the mesenchymal stem cells that have been described thus far is limited to cells of mesenchymal origin, including the best characterized mesenchymal stem cell (See Pittenger, et al. Science (1999) 284: 143-147 and U.S. Pat. No. 5,827,740 (SH2⁺ SH4⁺ CD29⁺ CD44⁺ CD71⁺ CD90⁺ CD106⁺ CD120a⁺ CD124⁺ CD14⁻ CD34⁻ CD45⁻)). The disclosure encompasses the use of various mesenchymal stem cells encompassed herein.

In one embodiment, MSC donor lots are generated from umbilical cord tissue. Means of generating umbilical cord tissue MSC have been previously published and are incorporated by reference [31-37]. The term "umbilical tissue derived cells (UTC)" refers, for example, to cells as described in U.S. Pat. Nos. 7,510,873, 7,413,734, 7,524,489, and 7,560,276. The UTC can be of any mammalian origin e.g. human, rat, primate, porcine and the like. In one embodiment of the disclosure, the UTC are derived from human umbilicus. Umbilicus-derived cells, which relative to a human cell that is a fibroblast, a mesenchymal stem cell, or an iliac crest bone marrow cell, have reduced expression of genes for one or more of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); *sine oculis* homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distal-less homeobox 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle). In addition, these isolated human umbilicus-derived cells express a gene for each of interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3, wherein the expression is increased relative to that of a human cell which is a fibroblast, a mesenchymal stem cell, an iliac crest bone marrow cell, or placenta-derived cell. The cells are capable of self-renewal and expansion in culture, and have the potential to differentiate into cells of other phenotypes.

Methods of deriving cord tissue mesenchymal stem cells from human umbilical tissue are provided. The cells are capable of self-renewal and expansion in culture, and have the potential to differentiate into cells of other phenotypes. The method comprises (a) obtaining human umbilical tissue; (b) removing substantially all of blood to yield a substantially blood-free umbilical tissue, (c) dissociating the tissue by mechanical or enzymatic treatment, or both, (d) resuspending the tissue in a culture medium, and (e) providing growth conditions which allow for the growth of a human umbilicus-derived cell capable of self-renewal and expansion in culture and having the potential to differentiate into cells of other phenotypes.

Tissue can be obtained from any completed pregnancy, term or less than term, whether delivered vaginally, or through other routes, for example surgical Cesarean section. Obtaining tissue from tissue banks is also considered within the scope of the present disclosure.

The tissue is rendered substantially free of blood by any means known in the art. For example, the blood can be physically removed by washing, rinsing, and diluting and the like, before or after bulk blood removal for example by suctioning or draining. Other means of obtaining a tissue substantially free of blood cells might include enzymatic or chemical treatment.

Dissociation of the umbilical tissues can be accomplished by any of the various techniques known in the art, including by mechanical disruption, for example, tissue can be aseptically cut with scissors, or a scalpel, or such tissue can be otherwise minced, blended, ground, or homogenized in any manner that is compatible with recovering intact or viable cells from human tissue.

In a present embodiment, the isolation procedure also utilizes an enzymatic digestion process. Many enzymes are known in the art to be useful for the isolation of individual cells from complex tissue matrices to facilitate growth in culture. As discussed above, a broad range of digestive enzymes for use in cell isolation from tissue is available to the skilled artisan. Ranging from weakly digestive (e.g. deoxyribonucleases and the neutral protease, dispase) to strongly digestive (e.g. papain and trypsin), such enzymes are available commercially. A nonexhaustive list of enzymes compatible herewith includes mucolytic enzyme activities, metalloproteases, neutral proteases, serine proteases (such as trypsin, chymotrypsin, or elastase), and deoxyribonucleases. Particular embodiments are enzyme activities selected from metalloproteases, neutral proteases and/or mucolytic activities. For example, collagenases are known to be useful for isolating various cells from tissues. Deoxyribonucleases can digest single-stranded DNA and can minimize cell-clumping during isolation. Enzymes can be used alone or in combination. Serine protease are preferably used in a sequence following the use of other enzymes as they may degrade the other enzymes being used. The temperature and time of contact with serine proteases must be monitored. Serine proteases may be inhibited with alpha 2 microglobulin in serum and therefore the medium used for digestion is preferably serum-free. EDTA and DNase are commonly used and may improve yields or efficiencies. Preferred methods involve enzymatic treatment with for example collagenase and dispase, or collagenase, dispase, and hyaluronidase, and such methods are provided wherein in certain preferred embodiments, a mixture of collagenase and the neutral protease dispase are used in the dissociating step. More preferred are those methods which employ digestion in the presence of at least one collagenase from *Clostridium histolyticum*, and either of the protease activities, dispase and thermolysin. Still more preferred are methods employing digestion with both collagenase and dispase enzyme activities. Also preferred are methods which include digestion with a hyaluronidase activity in addition to collagenase and dispase activities. The skilled artisan will appreciate that many such enzyme treatments are known in the art for isolating cells from various tissue sources. For example, the LIBERASE BLENDZYME (Roche) series of enzyme combinations of collagenase and neutral protease are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In other preferred embodiments, the tissue is incubated at 37° C. during the enzyme treatment of the dissociation step. Diluting the digest may also improve yields of cells as cells may be trapped within a viscous digest. While the use of enzyme is presently preferred, it is not required for isolation methods as provided herein. Methods based on mechanical separation alone may be successful in isolating the instant cells from the umbilicus as discussed above. The cells can be resuspended after the tissue is dissociated into any culture medium as discussed herein above. Cells may be resuspended following a centrifugation step to separate out the cells from tissue or other debris. Resuspension may involve mechanical methods of resuspending, or simply the addition of culture medium to the cells. Providing the growth conditions allows for a wide range of options as to culture medium, supplements, atmospheric conditions, and relative humidity for the cells. A particular temperature is 37° C., however the temperature may range from about 35° C. to 39° C. depending on the other culture conditions and desired use of the cells or culture.

Particular methods that provide cells that require no exogenous growth factors, except as are available in the supplemental serum provided with the Growth Medium, are encompassed herein. Also provided herein are methods of deriving umbilical cells capable of expansion in the absence of particular growth factors. The methods are similar to the method above, however they require that the particular growth factors (for which the cells have no requirement) be absent in the culture medium in which the cells are ultimately resuspended and grown in. In this sense, the method is selective for those cells capable of division in the absence of the particular growth factors. Particular cells in some embodiments are capable of growth and expansion in chemically-defined growth media with no serum added. In such cases, the cells may require certain growth factors, which can be added to the medium to support and sustain the cells. Particular factors to be added for growth on serum-free media include one or more of FGF, EGF, IGF, and PDGF. In some embodiments, two, three or all four of the factors are add to serum free or chemically defined media. In other embodiments, LIF is added to serum-free medium to support or improve growth of the cells.

Also provided are methods wherein the cells can expand in the presence of from about 5% to about 20% oxygen in their atmosphere. Methods to obtain cells that require L-valine require that cells be cultured in the presence of L-valine. After a cell is obtained, its need for L-valine can be tested and confirmed by growing on D-valine containing medium that lacks the L-isomer.

Methods are provided wherein the cells can undergo at least 25, 30, 35, or 40 doublings prior to reaching a senescent state. Methods for deriving cells capable of doubling to reach $10^{14}$ cells or more are provided. Preferred are those methods which derive cells that can double sufficiently to produce at least about $10^{14}$, $10^{15}$, $10^{16}$, or $10^{17}$ or more cells when seeded at from about $10^3$ to about $10^6$ cells/cm$^2$ in culture. In particular cases, these cell numbers are produced within 80, 70, or 60 days or less. In one embodiment, cord tissue mesenchymal stem cells are isolated and expanded, and possess one or more markers selected from a group comprising of CD10, CD13, CD44, CD73, CD90, CD141, PDGFr-alpha, or HLA-A, B, C. In addition, the cells do not produce one or more of CD31, CD34, CD45, CD117, CD141, or HLA-DR, DP, DQ.

In order to determine the quality of MSC cultures, flow cytometry is performed on all cultures for surface expression of SH-2, SH-3, SH-4 MSC markers and lack of contaminating CD14- and CD-45 positive cells. Cells were detached with 0.05% trypsin-EDTA, washed with DPBS+2% bovine albumin, fixed in 1% paraformaldehyde, blocked in 10% serum, incubated separately with primary SH-2, SH-3 and SH-4 antibodies followed by PE-conjugated anti-mouse IgG(H+L) antibody. Confluent MSC in 175 cm$^2$ flasks are washed with Tyrode's salt solution, incubated with medium 199 (M199) for 60 min, and detached with 0.05% trypsin-EDTA (Gibco). Cells from 10 flasks were detached at a time and MSCs were resuspended in 40 ml of M199+1% human serum albumin (HSA; American Red Cross, Washington D.C., USA). MSCs harvested from each 10-flask set were stored for up to 4 h at 4° C. and combined at the end of the harvest. A total of 2-10'$10^6$ MSC/kg were resuspended in M199+1% HSA and centrifuged at 460 g for 10 min at 20° C. Cell pellets were resuspended in fresh M199+1% HSA media and centrifuged at 460 g for 10 min at 20° C. for three additional times. Total harvest time was 2-4 h based on MSC yield per flask and the target dose. Harvested MSC were cryopreserved in Cryocyte (Baxter, Deerfield, Ill., USA) freezing bags using a rate controlled freezer at a final concentration of 10% DMSO (Research Industries, Salt Lake City, Utah, USA) and 5% HSA. On the day of infusion cryopreserved units were thawed at the bedside in a 37° C. water bath and transferred into 60 ml syringes within 5 min and infused intravenously into patients over 10-15 min. Patients are premedicated with 325-650 mg acetaminophen and 12.5-25 mg of diphenhydramine orally. Blood pressure, pulse, respiratory rate, temperature and oxygen saturation are monitored at the time of infusion and every 15 min thereafter for 3 h followed by every 2 h for 6 h.

In one embodiment, MSC are generated according to protocols previously utilized for treatment of patients utilizing bone marrow derived MSC. Specifically, bone marrow is aspirated (10-30 ml) under local anesthesia (with or without sedation) from the posterior iliac crest, collected into sodium heparin containing tubes and transferred to a Good Manufacturing Practices (GMP) clean room. Bone marrow cells are washed with a washing solution such as Dulbecco's phosphate-buffered saline (DPBS), RPMI, or PBS supplemented with autologous patient plasma and layered on to 25 ml of Percoll (1.073 g/ml) at a concentration of approximately $1-2\times10^7$ cells/ml. Subsequently the cells are centrifuged at 900 g for approximately 30 min or a time period sufficient to achieve separation of mononuclear cells from debris and erythrocytes. Said cells are then washed with PBS and plated at a density of approximately $1\times10^6$ cells per ml in 175 cm² tissue culture flasks in DMEM with 10% FCS with flasks subsequently being loaded with a minimum of 30 million bone marrow mononuclear cells. The MSCs are allowed to adhere for 72 h followed by media changes every 3-4 days. Adherent cells are removed with 0.05% trypsin-EDTA and replated at a density of 1'10⁶ per 175 cm². The bone marrow MSC may be administered intravenously, or in a particular embodiment, intrathecally in a patient suffering radiation associated neurodegenerative manifestations. Although doses may be determined by one of skill in the art, and are dependent on various patient characteristics, intravenous administration may be performed at concentrations ranging from 1-10 million MSC per kilogram, with a preferred dose of approximately 2-5 million cells per kilogram.

In one embodiment, hematopoietic stem cells are CD34+ cells isolated from the peripheral blood, bone marrow, or umbilical cord blood. Specifically, the hematopoietic stem cells may be derived from the blood system of mammalian animals, include but not limited to human, mouse, rat, and these hematopoietic stem cells may be harvested by isolating from the blood or tissue organs in mammalian animals. Hematopoietic stem cells may be harvested from a donor by any known methods in the art. For example, U.S. Pub. 2013/0149286 details procedures for obtaining and purifying stem cells from mammalian cadavers. Stem cells may be harvested from a human by bone marrow harvest or peripheral blood stem cell harvest, both of which are well known techniques in the art. After stem cells have been obtained from the source, such as from certain tissues of the donor, they may be cultured using stem cell expansion techniques. Stem cell expansion techniques are disclosed in U.S. Pat. No. 6,326,198 to Emerson et al., entitled "Methods and compositions for the ex vivo replication of stem cells, for the optimization of hematopoietic progenitor cell cultures, and for increasing the metabolism, GM-CSF secretion and/or IL-6 secretion of human stromal cells," issued Dec. 4, 2001; U.S. Pat. No. 6,338,942 to Kraus et al., entitled "Selective expansion of target cell populations," issued Jan. 15, 2002; and U.S. Pat. No. 6,335,195 to Rodgers et al., entitled "Method for promoting hematopoietic and cell proliferation and differentiation," issued Jan. 1, 2002, which are hereby incorporated by reference in their entireties. In some embodiments, stem cells obtained from the donor are cultured in order to expand the population of stem cells. In other preferred embodiments, stem cells collected from donor sources are not expanded using such techniques. Standard methods can be used to cyropreserve the stem cells.

In some embodiments of the disclosure, where there are risks associated with particular types of stem cells, for example, pluripotent stem cells, the stem cells may be encapsulated by membranes, as well as capsules, prior to implantation. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval. A wide variety of materials may be used in various embodiments for microencapsulation of stem cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. Techniques for micro-encapsulation of cells that may be used for administration of stem cells are known to those of skill in the art and are described, for example, in Chang, P., et al., 1999; Matthew, H. W., et al., 1991; Yanagi, K., et al., 1989; Cal Z. H., et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of stem cells. Certain embodiments incorporate stem cells into a polymer, such as a biopolymer or synthetic polymer. Examples of biopolymers include, but are not limited to, fibronectin, fibrin, fibrinogen, thrombin, collagen, and proteoglycans. Other factors, such as the cytokines discussed above, can also be incorporated into the polymer. In other embodiments of the invention, stem cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 2:
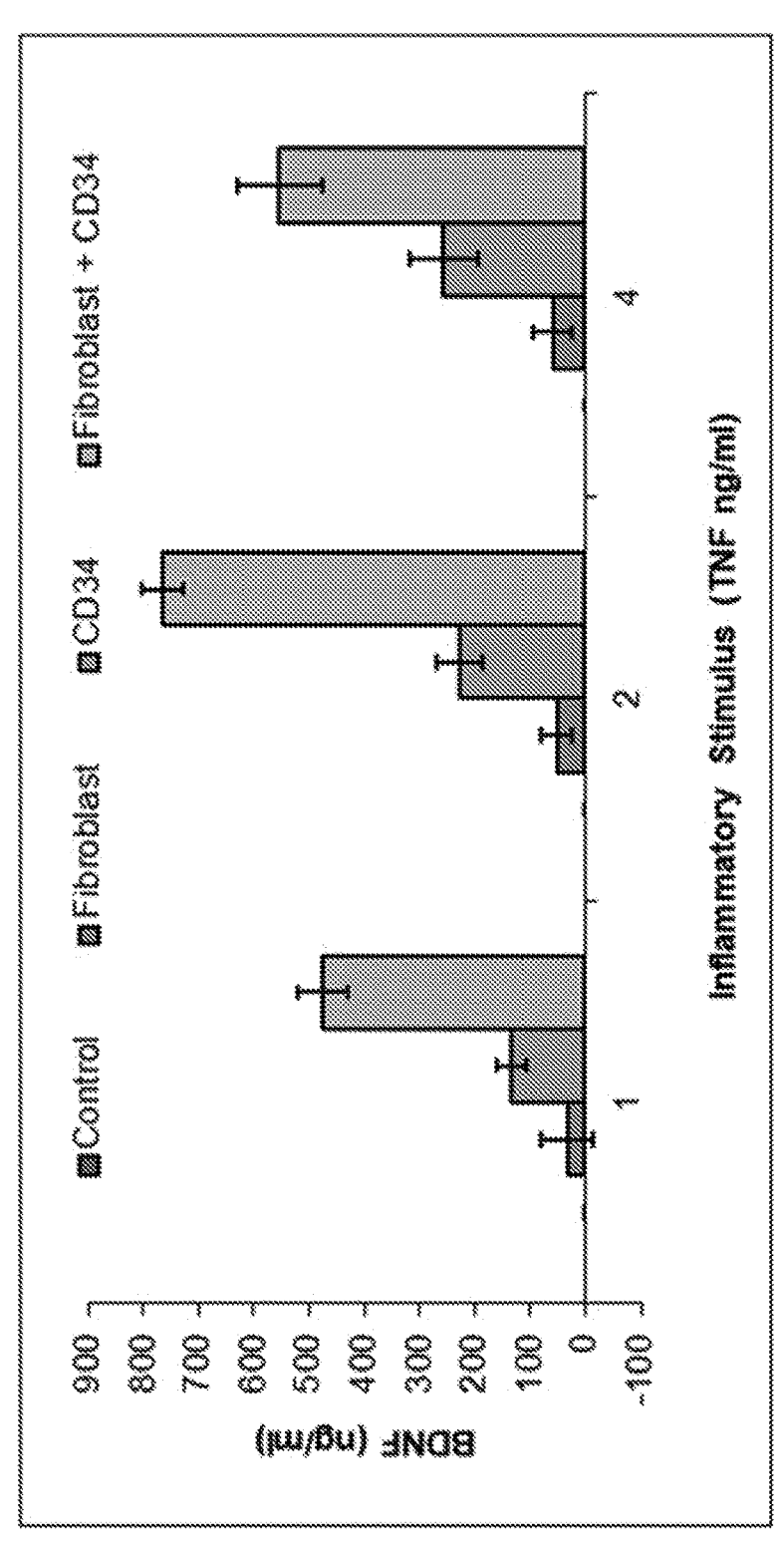
FIG. 2 shows that fibroblasts synergize with CD34 at producing BDNF. The bars from left to right are control, fibroblasts alone, CD34 alone, and a mixture of fibroblasts and CD34.
Figure 3:
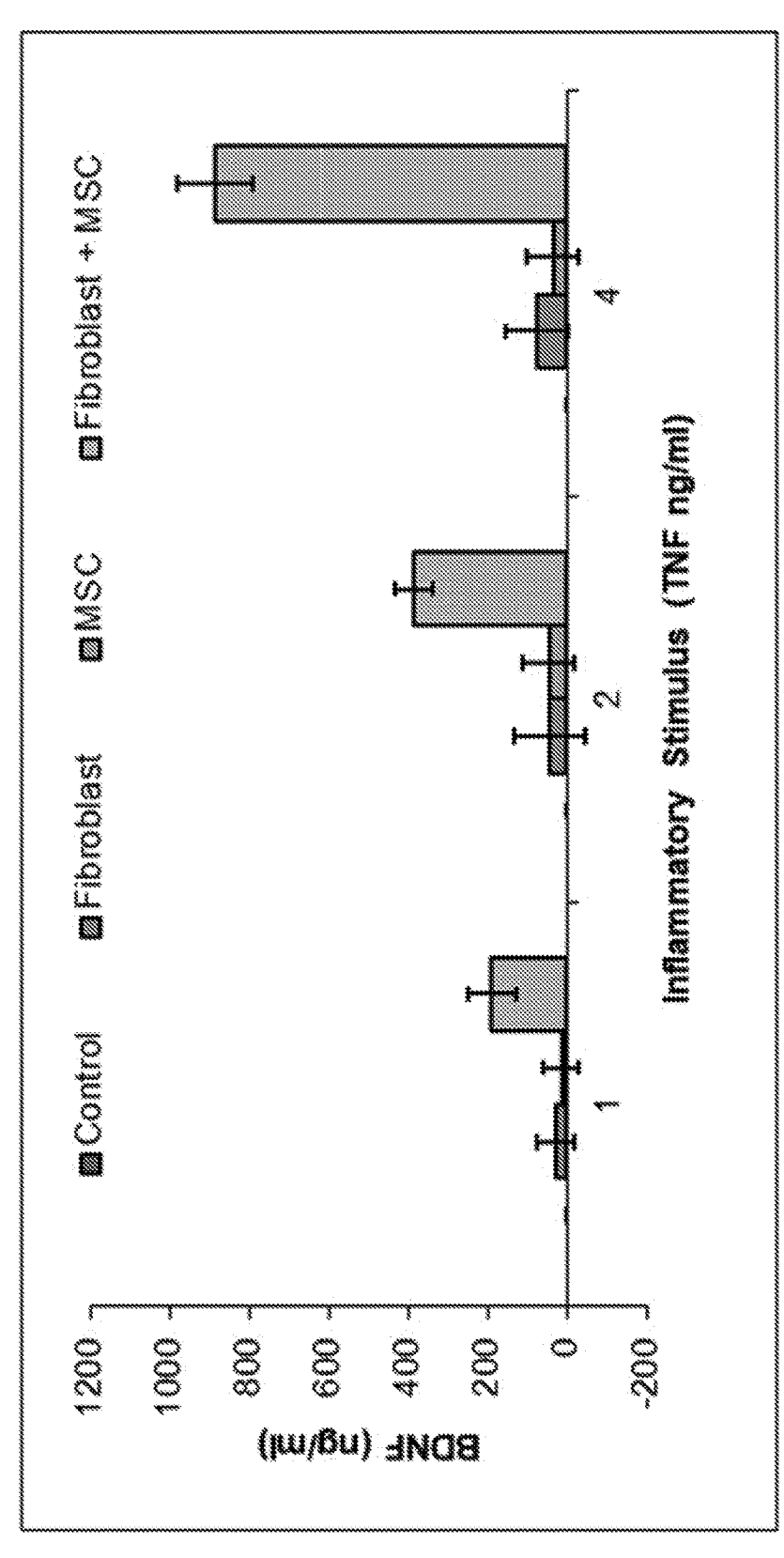
FIG. 3 demonstrates that fibroblasts synergize with MSCs at producing BDNF. The bars from left to right are control, fibroblasts alone, MSCs alone, and a mixture of fibroblasts and MSCs.

Stimulation of Neuroregenerative Cytokine BDNF in Response to Inflammation by Fibroblast and Fibroblast Combinations Fibroblasts were co-cultured at 1:1 ratio with either monocytes, mesenchymal stem cells, or hematopoietic stem cells. Cells were cultured for 48 hours in the presence of increasing concentrations of TNF-alpha to stimulate inflammatory signaling. Presence of BDNF was determined by ELISA. As can be seen in FIGS. 1-3, all combinations of cells resulted in additive or synergistic increases in production of this neuroprotective cytokine.

Example 2

Figure 4:
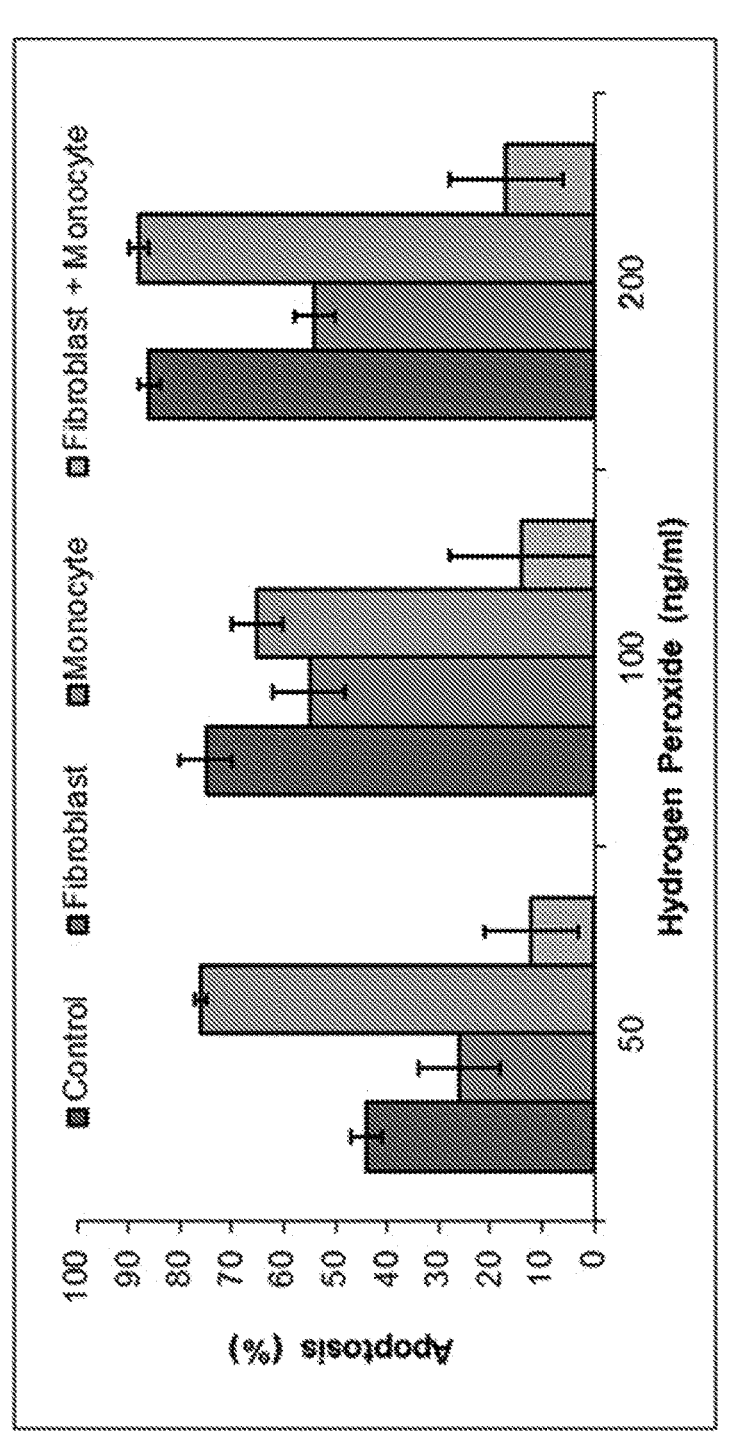
FIG. 4 shows that fibroblasts synergize with monocytes to inhibit neuron death. The bars from left to right are control, fibroblasts alone, monocytes alone, and a mixture of fibroblasts and monocytes.
Figure 5:
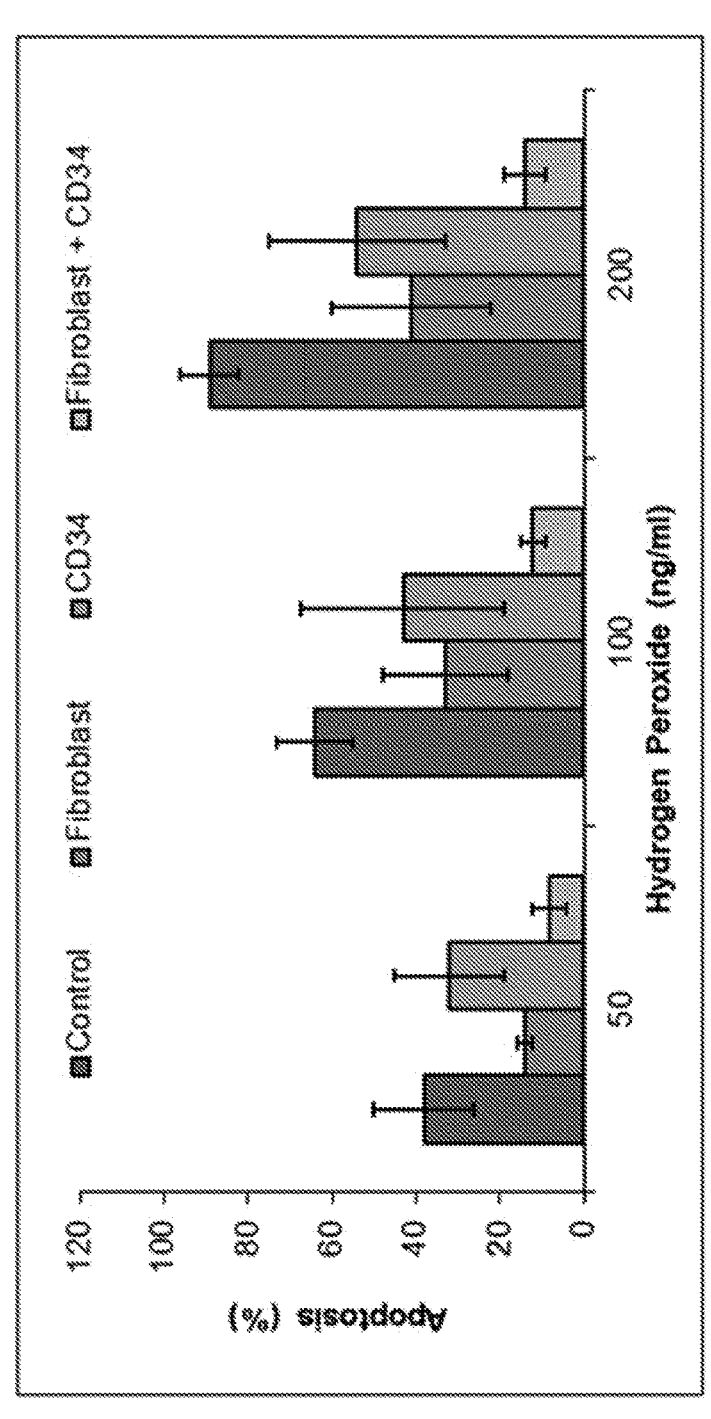
FIG. 5 shows that fibroblasts synergize with CD34 to inhibit neuron death. The bars from left to right are control, fibroblasts alone, CD34 alone, and a mixture of fibroblasts and CD34.
Figure 6:
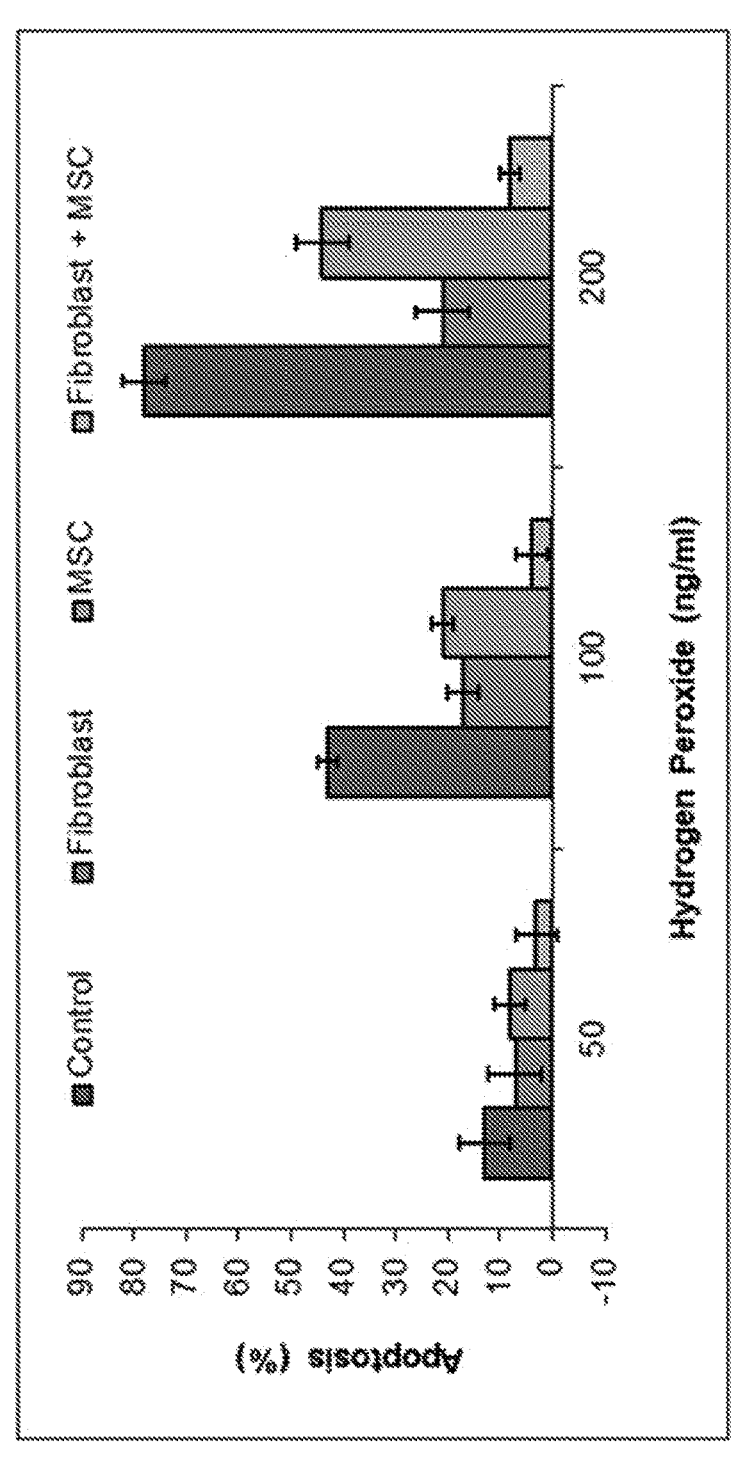
FIG. 6 shows that fibroblasts synergize with MSCs to inhibit neuron death. The bars from left to right are control, fibroblasts alone, MSCs alone, and a mixture of fibroblasts and MSCs.

Reduction of Neuron Apoptosis in Response to Oxidative Stress by Fibroblast and Fibroblast Combinations Fibroblasts were co-cultured at 1:1 ratio with either monocytes, mesenchymal stem cells, or hematopoietic stem cells. Cells were cultured for 48 hours in the presence of increasing concentrations of hydrogen peroxide to stimulate oxidative stress. Conditioned media from cells was added for 48 hours to neurons cultured in the same concentration of hydrogen peroxide. Apoptosis was measured by flow cytometry using Annexin V staining and presenting as % of apoptotic cells. Fibroblasts synergize with monocytes (FIG. 4), CD34 (FIG. 5), or MSC (FIG. 6) to inhibit neuron death.

Example 3

Figure 7:
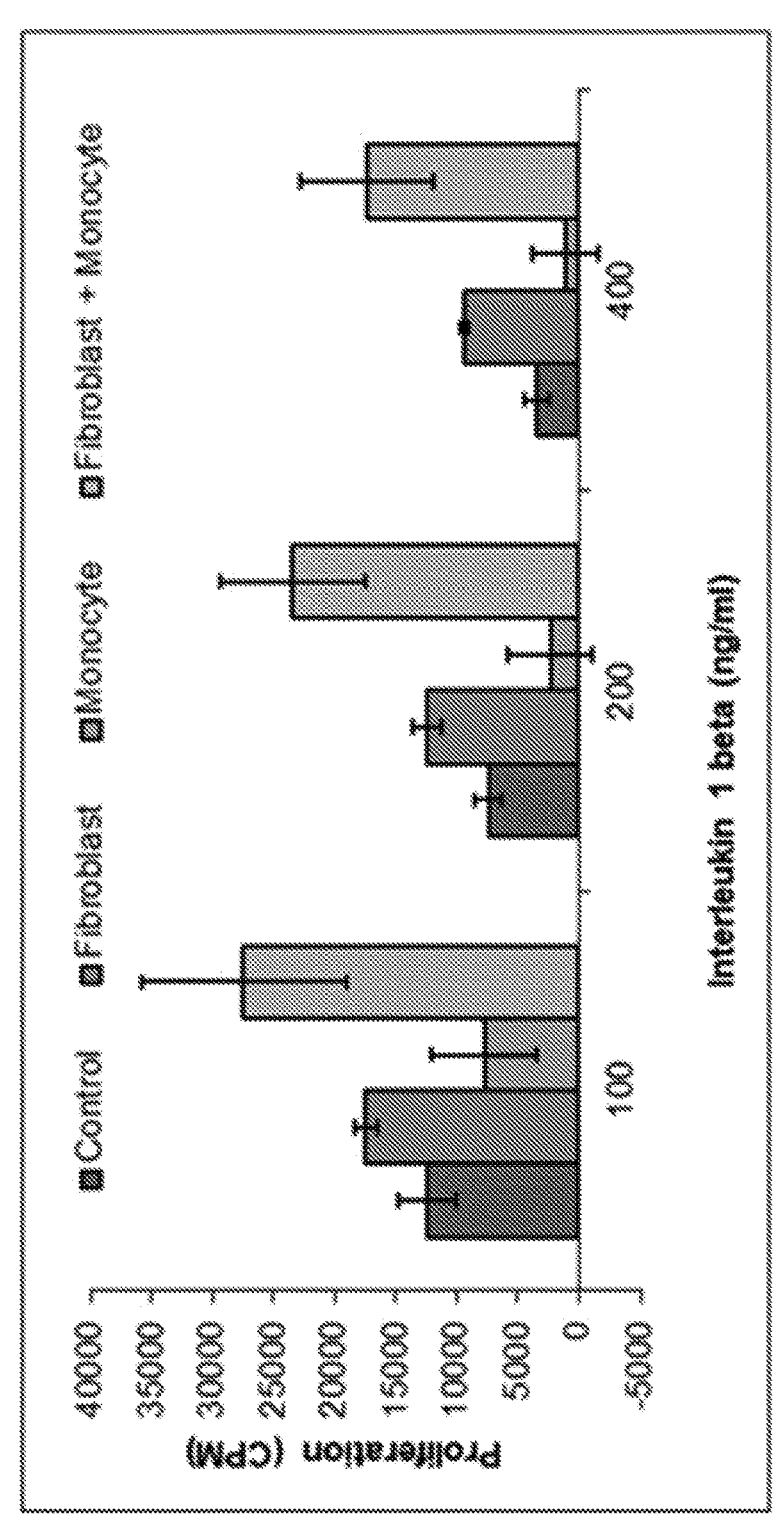
FIG. 7 demonstrates that fibroblasts synergize with monocytes to stimulate neurogenesis. The bars from left to right are control, fibroblasts alone, monocytes alone, and a mixture of fibroblasts and monocytes.
Figure 8:
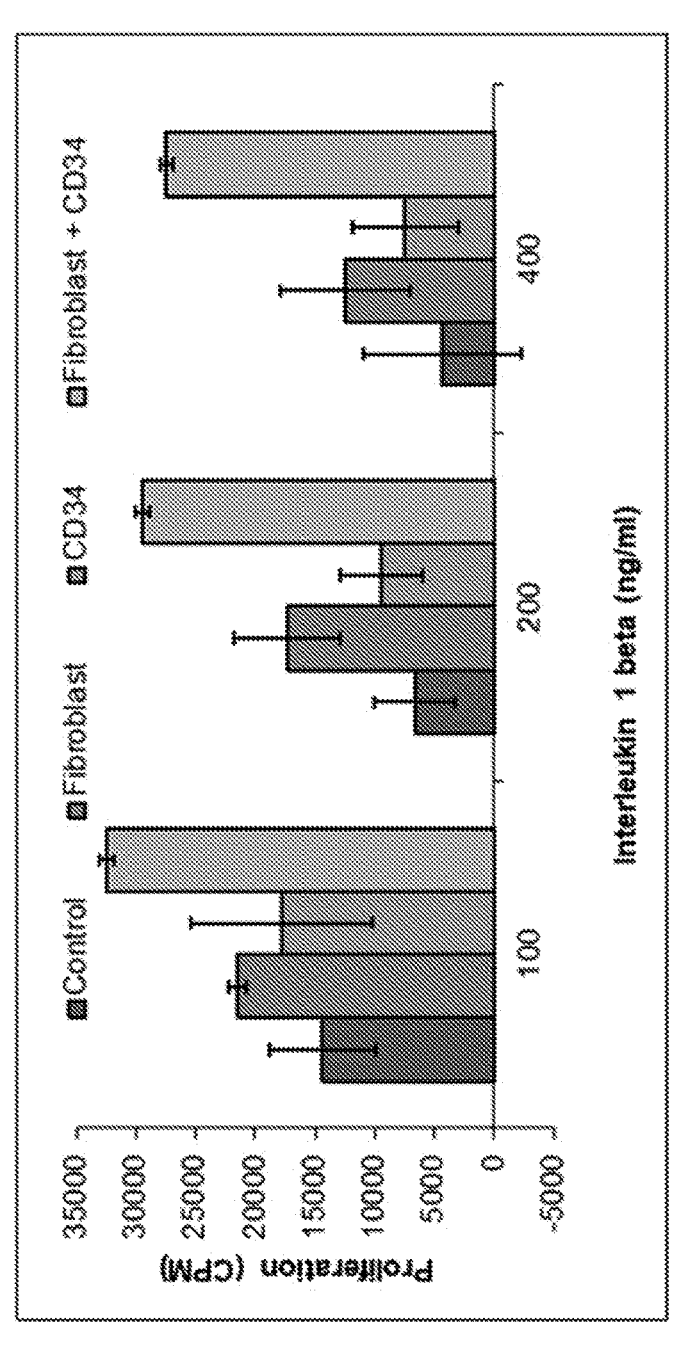
FIG. 8 shows that fibroblasts synergize with CD34 to stimulate neurogenesis. The bars from left to right are control, fibroblasts alone, CD34 alone, and a mixture of fibroblasts and CD34.
Figure 9:
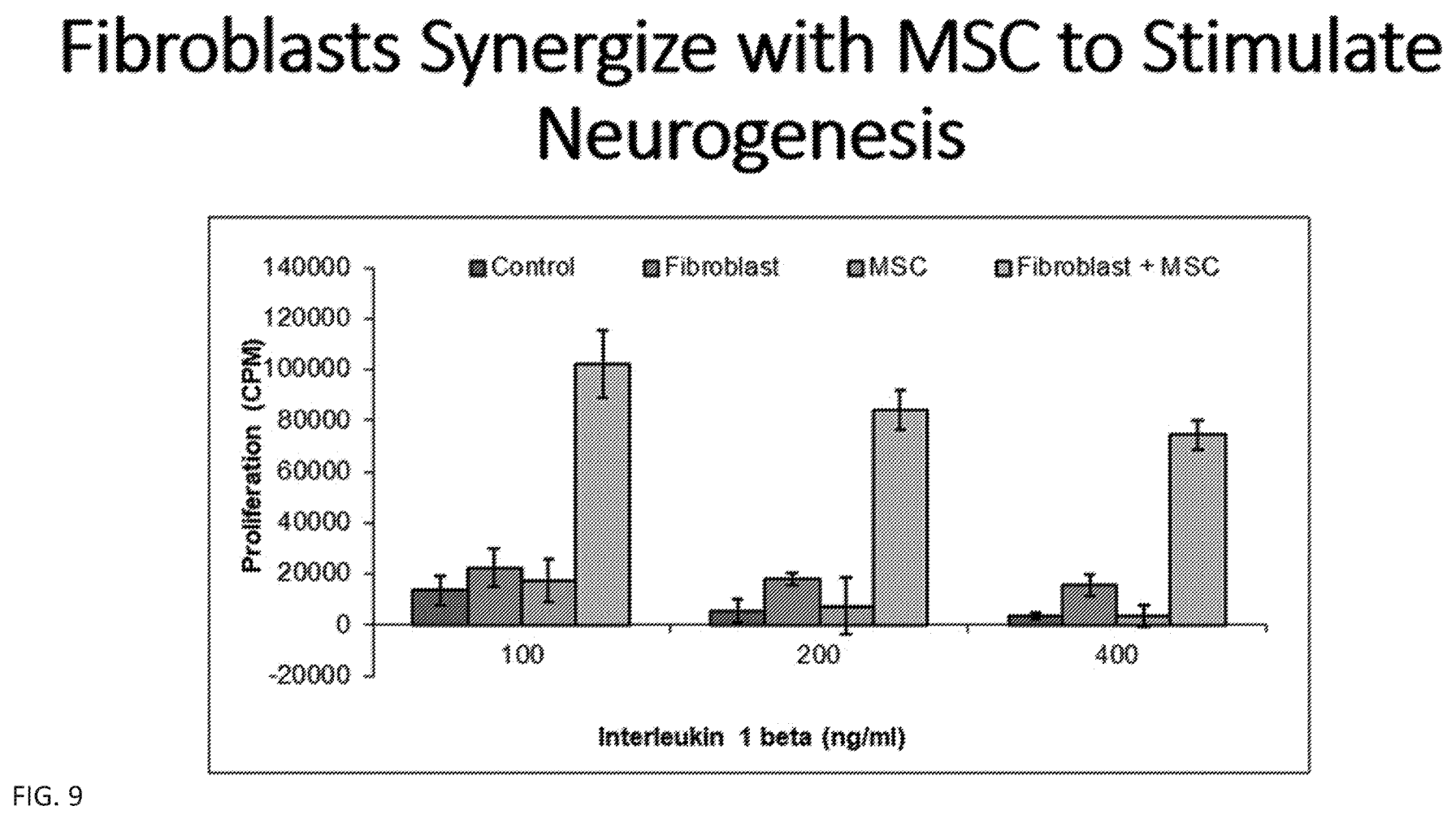

Stimulation of Neural Progenitor Cell Proliferation by Fibroblasts and Fibroblast Cell Combinations Fibroblasts were co-cultured at 1:1 ratio with either monocytes, mesenchymal stem cells, or hematopoietic stem cells. Cells were cultured for 48 hours in the presence of increasing concentrations of interleukin-1 beta to stimulate production of mitogenic factors. Conditioned media from cells was added for 48 hours to neural progenitor cells cultured and proliferation was measured by thymidine incorporation for 48 hours. Fibroblasts synergize with monocytes (FIG. 7), CD34 (FIG. 8), or MSCs (FIG. 9) to stimulate neurogenesis.

Example 4

Fibroblast Conditioned Media Protects Neurons from Injury

SH-SYSY cells (Sigma), which are a thrice-cloned subline of bone marrow biopsy-derived line SK-N-SH, are known to possess dopamine-β-hydroxylase activity and can convert glutamate to the neurotransmitter GABA. These cells serve as a model for neurotoxicity when treated with 70 mM glucose for 24 hours which leads to approximately 70% apoptosis. In order to assess whether fibroblasts possessed neuroprotective effects, increasing concentration of fibroblast conditioned media was added to SH-SYSY cells.

To obtain fibroblast-conditioned media, dermal fibroblasts (ATCC) were cultured in OPTI-MEM media with 10% fetal calf serum and non-essential amino acids for 24 hours. Cells were cultured in T-75 flasks at confluency with 5 ml media. Fibroblast-conditioned media was generated by extracting liquid media after 24 hours.

Figure 10:
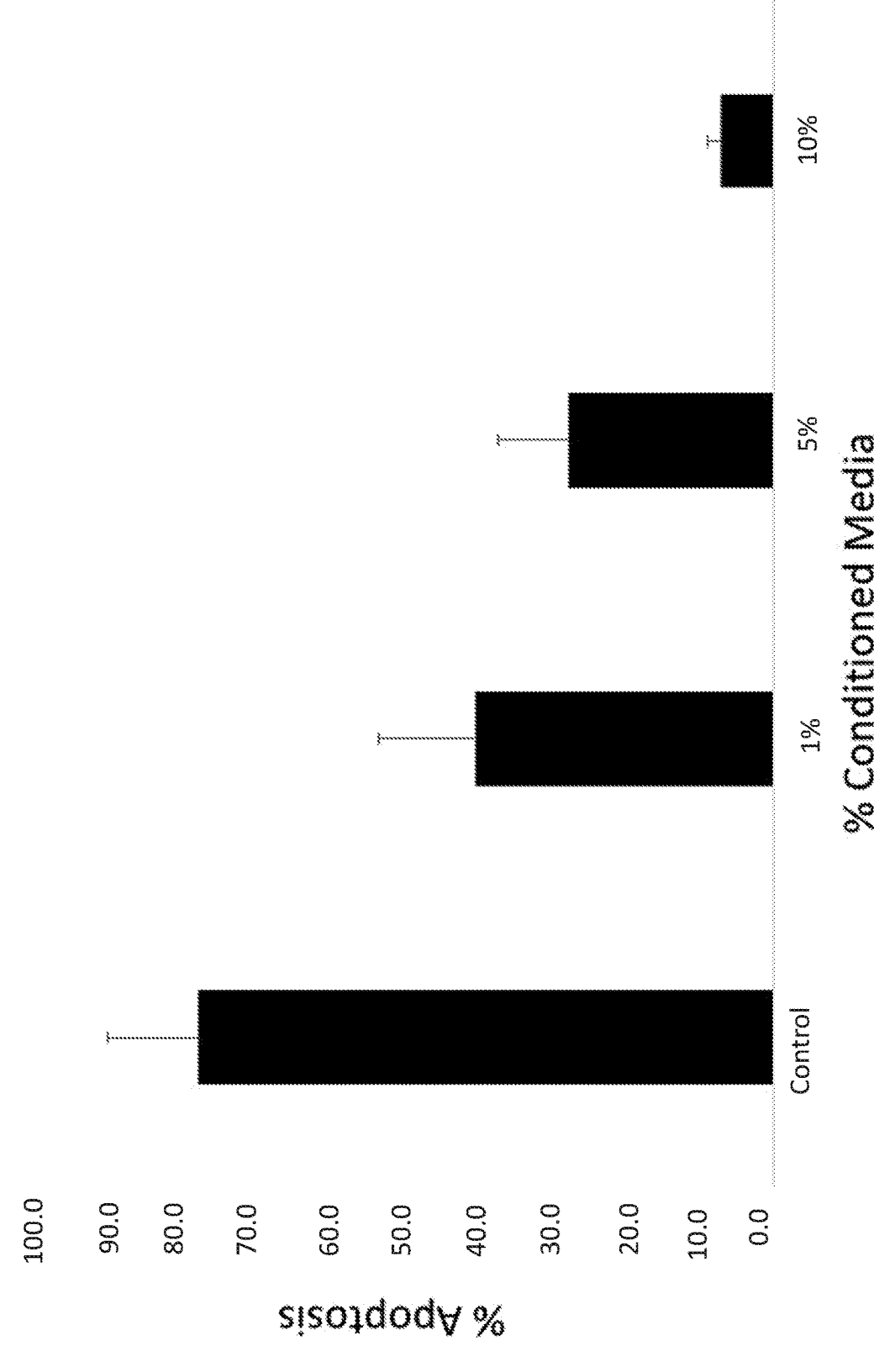
FIG. 10 shows that fibroblast-conditioned media protects neurons from injury.

A dose-dependent reduction of glucose-induced neuronal death was observed by administration of conditioned media, as assessed by Annexin-V staining (FIG. 10).

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

U.S. Pat. No. 4,353,888
U.S. Pat. No. 4,744,933
U.S. Pat. No. 4,749,620
U.S. Pat. No. 4,814,274
U.S. Pat. No. 5,084,350
U.S. Pat. No. 5,089,272
U.S. Pat. No. 5,578,442
U.S. Pat. No. 5,639,275
U.S. Pat. No. 5,676,943
U.S. Pat. No. 5,827,740

U.S. Pat. No. 7,413,734
U.S. Pat. No. 7,510,873
U.S. Pat. No. 7,524,489
U.S. Pat. No. 7,560,276
European Patent Publication No. 301,777

1. Zhuo, Y., et al., *White matter impairment in type 2 diabetes mellitus with and without microvascular disease.* Neuroimage Clin, 2019. 24: p. 101945.
2. Mendez, M. F., *The neuropsychiatric aspects of boxing.* Int J Psychiatry Med, 1995. 25(3): p. 249-62.
3. Jordan, B. D., *Neurologic aspects of boxing.* Arch Neurol, 1987. 44(4): p. 453-9.
4. McKee, A. C., et al., *Chronic traumatic encephalopathy in athletes: progressive tauopathy after repetitive head injury.* J Neuropathol Exp Neurol, 2009. 68(7): p. 709-35.
5. Gavett, B. E., et al., *Clinical appraisal of chronic traumatic encephalopathy: current perspectives and future directions.* Curr Opin Neurol, 2011. 24(6): p. 525-31.
6. Stern, R. A., et al., *Long-term consequences of repetitive brain trauma: chronic traumatic encephalopathy.* PM R, 2011. 3(10 Suppl 2): p. S460-7.
7. McCrory, P., T. Zazryn, and P. Cameron, *The evidence for chronic traumatic encephalopathy in boxing.* Sports Med, 2007. 37(6): p. 467-76.
8. Bouziane, C., et al., *White Matter by Diffusion MRI Following Methylphenidate Treatment: A Randomized Control Trial in Males with Attention-Deficit/Hyperactivity Disorder.* Radiology, 2019: p. 182528.
9. Kochunov, P., et al., *White Matter in Schizophrenia Treatment Resistance. Am J Psychiatry,* 2019: p. appiajp201918101212.
10. Herweh, C., et al., *Reduced white matter integrity in amateur boxers. Neuroradiology,* 2016. 58(9): p. 911-20.
11. Foster, J. B., R. Leiguarda, and P. J. Tilley, *Brain damage in National Hunt jockeys.* Lancet, 1976. 1(7967): p. 981-3.
12. McCrory, P., M. Turner, and J. Murray, *A punch drunk jockey?* Br J Sports Med, 2004. 38(3): p. e3.
13. Berstad, J. R., et al., *Whiplash: chronic organic brain syndrome without hydrocephalus ex vacuo.* Acta Neurol Scand, 1975. 51(4): p. 268-84.
14. Squier, W., *Shaken baby syndrome: the quest for evidence.* Dev Med Child Neurol, 2008. 50(1): p. 10-4.
15. Omalu, B. I., et al., *Chronic traumatic encephalopathy in a professional American wrestler.* J Forensic Nurs, 2010. 6(3): p. 130-6.
16. Omalu, B., et al., *Chronic traumatic encephalopathy in an Iraqi war veteran with posttraumatic stress disorder who committed suicide.* Neurosurg Focus, 2011. 31(5): p. E3.
17. Hasoon, J., *Blast-associated traumatic brain injury in the military as a potential trigger for dementia and chronic traumatic encephalopathy.* US Army Med Dep J, 2017(1-17): p. 102-105.
18. Omalu, B. I., et al., *Chronic traumatic encephalopathy in a National Football League player.* Neurosurgery, 2005. 57(1): p. 128-34; discussion 128-34.
19. Omalu, B. I., et al., *Chronic traumatic encephalopathy in a national football league player: part II. Neurosurgery,* 2006. 59(5): p. 1086-92; discussion 1092-3.
20. Breedlove, E. L., et al., *Biomechanical correlates of symptomatic and asymptomatic neurophysiological impairment in high school football.* J Biomech, 2012. 45(7): p. 1265-72.
21. Maroon, J. C., et al., *Chronic traumatic encephalopathy in contact sports: a systematic review of all reported pathological cases.* PLoS One, 2015. 10(2): p. e0117338.

22. Bieniek, K. F., et al., *Association between contact sports participation and chronic traumatic encephalopathy: a retrospective cohort study*. Brain Pathol, 2019.

23. McMillan, T. M., et al., *Long-term health outcomes after exposure to repeated concussion in elite level: rugby union players*. J Neurol Neurosurg Psychiatry, 2017. 88(6): p. 505-511.

24. Ling, H., et al., *Mixed pathologies including chronic traumatic encephalopathy account for dementia in retired association football (soccer) players*. Acta Neuropathol, 2017. 133(3): p. 337-352.

25. Nitrini, R., *Soccer (Football Association) and chronic traumatic encephalopathy: A short review and recommendation*. Dement Neuropsychol, 2017. 11(3): p. 218-220.

26. Siegler, A., et al., *Head Trauma in Jail and Implications for Chronic Traumatic Encephalopathy in the United States: Case Report and Results of Injury Surveillance in NYC Jails*. J Health Care Poor Underserved, 2017. 28(3): p. 1042-1049.

27. Tribett, T., et al., *Chronic Traumatic Encephalopathy Pathology After Shotgun Injury to the Brain*. J Forensic Sci, 2019. 64(4): p. 1248-1252.

28. Lim, L. J. H., R. C. M. Ho, and C. S. H. Ho, *Dangers of Mixed Martial Arts in the Development of Chronic Traumatic Encephalopathy*. Int J Environ Res Public Health, 2019. 16(2).

29. Mez, J., et al., *Clinicopathological Evaluation of Chronic Traumatic Encephalopathy in Players of American Football*. JAMA, 2017. 318(4): p. 360-370.

30. Alosco, M. L., et al., *Age of first exposure to tackle football and chronic traumatic encephalopathy*. Ann Neurol, 2018. 83(5): p. 886-901.

31. Van Pham, P., et al., *Isolation and proliferation of umbilical cord tissue derived mesenchymal stem cells for clinical applications*. Cell Tissue Bank, 2015.

32. Fazzina, R., et al., *A new standardized clinical-grade protocol for banking human umbilical cord tissue cells*. Transfusion, 2015. 55(12): p. 2864-73.

33. Bieback, K., *Platelet lysate as replacement for fetal bovine serum in mesenchymal stromal cell cultures*. Transfus Med Hemother, 2013. 40(5): p. 326-35.

34. Stanko, P., et al., *Comparison of human mesenchymal stem cells derived from dental pulp, bone marrow, adipose tissue, and umbilical cord tissue by gene expression*. Biomed Pap Med Fac Univ Palacky Olomouc Czech Repub, 2014. 158(3): p. 373-7.

35. Schira, J., et al., *Significant clinical, neuropathological and behavioural recovery from acute spinal cord trauma by transplantation of a well-defined somatic stem cell from human umbilical cord blood*. Brain, 2012. 135(Pt 2): p. 431-46.

36. Hartmann, I., et al., *Umbilical cord tissue-derived mesenchymal stem cells grow best under GMP-compliant culture conditions and maintain their phenotypic and functional properties*. J Immunol Methods, 2010. 363(1): p. 80-9.

37. Friedman, R., et al., *Umbilical cord mesenchymal stem cells: adjuvants for human cell transplantation*. Biol Blood Marrow Transplant, 2007. 13(12): p. 1477-8.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of treating a sub-concussive or concussive brain injury in an individual, comprising the steps of: a) optionally identifying an individual with one or more elevated inflammatory markers subsequent to a head and/or neck injury; b) administering a therapeutically sufficient amount of regenerative cells and/or one or more products derived from said regenerative cells;

wherein said regenerative cells comprise fibroblasts, fibroblasts and hematopoietic stem cells (HSCs), fibroblasts and mesenchymal stem cells (MSCs), and/or fibroblasts and monocytes, wherein the inflammatory markers are selected from the group consisting of: a) C-reactive protein; b) interleukin-1; c) interleukin-6; d) interleukin-8; e) interleukin-33; f) erythrocyte sedimentation ratio; g) TNF-alpha; h) interferon-gamma; and i) a combination thereof, wherein the inflammatory markers are elevated compared to an individual without a sub-concussive or concussive brain injury or a value in the general population, wherein the one or more products derived from said regenerative cells comprise conditioned media, cellular lysate, apoptotic bodies, exosomes, microvesicles, or a combination thereof.

2. The method of claim 1, wherein the inflammatory markers are elevated at least 20% higher as compared to an individual without a sub-concussive or concussive brain injury or the value in the general population.

3. The method of claim 1, wherein said regenerative cells are fibroblasts.

4. The method of claim 3, wherein said fibroblast cells express a marker selected from the group consisting of Oct-4, Nanog, Sox-2, KLF4, c-Myc, Rex-1, GDF-3, LIF receptor, CD105, CD117, CD344 Stella, and a combination thereof.

5. The method of claim 3, wherein the fibroblast cells express a marker selected from the group consisting of CD10, CD13, CD44, CD73, CD90, CD141, PDGFr-alpha, HLA-A, HLA-B, HLA-C, and a combination thereof.

6. The method of claim 3, wherein the fibroblast cells do not express a marker selected from the group consisting of MHC class I, MHC class II, CD45, CD13, CD49c, CD66b, CD73, CD105, CD90, and a combination thereof.

7. The method of claim 3, wherein the fibroblast cells do not express a marker selected from the group consisting of CD31, CD34, CD45, CD117, CD141, HLA-DR, HLA-DP, HLA-DQ, and a combination thereof.

8. The method of claim 1, wherein said regenerative cells are a combination of fibroblasts with hematopoietic stem cells.

9. The method of claim 8, wherein said hematopoietic stem cells are capable of multi-lineage reconstitution in an immunodeficient host.

10. The method of claim 8, wherein said hematopoietic stem cells express the c-kit protein.

11. The method of claim 8, wherein said hematopoietic stem cells express the Sca-1 protein, express CD34, express CD133, lack expression of lineage markers, and/or lack expression of CD38.

12. The method of claim 8, wherein said hematopoietic stem cells are positive for expression of c-kit and Sca-1 and substantially lack expression of lineage markers.

13. The method of claim 8, wherein said hematopoietic stem cells are derived from a) peripheral blood; b) mobilized peripheral blood; c) bone marrow; d) cord blood; e) adipose stromal vascular fraction; f) derived from progenitor cells; or g) a combination thereof.

14. The method of claim 1, wherein said regenerative cells comprise mesenchymal stem cells and fibroblasts.

15. The method of claim 14, wherein said mesenchymal stem cells (a) express a marker selected from the group consisting of: a) CD73; b) CD90; c) CD105; and d) a combination thereof;

(b) lack expression of a marker selected from the group consisting of: a) CD14; b) CD45; c) CD34; and d) a combination thereof; and/or (c) are plastic adherent.

16. The method of claim 14, wherein said mesenchymal stem cells are derived from tissues selected from the group consisting of: a) bone marrow; b) peripheral blood; c) adipose tissue; d) mobilized peripheral blood; e) umbilical cord blood; f) Wharton's jelly; g) umbilical cord tissue; h) skeletal muscle tissue; i) subepithelial umbilical cord tissue; j) endometrial tissue; k) menstrual blood; 1) fallopian tube tissue; and m) a combination thereof.

17. The method of claim 16, wherein said mesenchymal stem cells (a) are from umbilical cord tissue and express markers selected from the group consisting of: a) oxidized low density lipoprotein receptor 1, b) chemokine receptor ligand 3; c) granulocyte chemotactic protein; and d) a combination thereof; and/or (b) are from umbilical cord tissue and do not express markers selected from the group consisting of: a) CD117; b) CD31; c) CD34; d) CD45; and e) a combination thereof; and/or (c) are from umbilical cord tissue and express, relative to a human fibroblast, increased levels of interleukin 8 and/or reticulon 1; and/or (d) are from umbilical cord tissue and have the potential to differentiate into cells of at least a skeletal muscle, vascular smooth muscle, pericyte or vascular endothelium phenotype; and/or (e) are from umbilical cord tissue and express markers selected from the group consisting of: a) CD10; b) CD13; c) CD44; d) CD73; e) CD90; and f) a combination thereof.

18. The method of claim 16, wherein said umbilical cord tissue mesenchymal stem cell is an isolated umbilical cord tissue cell isolated from umbilical cord tissue substantially free of blood that is capable of self-renewal and expansion in culture.

19. The method of claim 16, wherein said umbilical cord tissue mesenchymal stem cells have the potential to differentiate into cells of other phenotypes.

20. The method of claim 19, wherein said other phenotypes comprise: a) osteocytic; b) adipogenic; c) chondrogenic differentiation or d) a combination thereof.

21. The method of claim 16, wherein (a) said cord tissue-derived mesenchymal stem cells can undergo or has undergone at least 20 doublings in culture;

(b) said cord tissue-derived mesenchymal stem cell maintains a normal karyotype upon passaging;

(c) expresses a marker selected from the group consisting of: a) CD10 b) CD13; c) CD44; d) CD73; e) CD90; f) PDGFr-alpha; g) PD-L2; h) HLA-A,B,C; and i) a combination thereof;

(d) do not express one or more markers selected from the group consisting of a) CD31; b) CD34; c) CD45; d) CD80; e) CD86; f) CD117; g) CD141; h) CD178; i) B7-H2; j) HLA-G; k) HLA-DR,DP,DQ; and 1) a combination thereof;

(e) secretes factors selected from the group consisting of: a) MCP-1; b) MIP1beta; c) IL-6; d) IL-8; e) GCP-2; f) HGF; g) KGF; h) FGF; i) HB-EGF; j) BDNF; k) TPO; 1) RANTES; m) TIMP1; and n) a combination thereof;

(f) express markers selected from the group consisting of: a) TRA1-60; b) TRA1-81; c) SSEA3; d) SSEA4; e) NANOG; and f) a combination thereof;

(g) are positive for alkaline phosphatase staining; and/or (h) are capable of differentiating into one or more lineages selected from the group consisting of a) ectoderm; b) mesoderm; c) endoderm; and d) a combination thereof.

22. The method of claim 16, wherein (a) said bone marrow-derived mesenchymal stem cells possess markers selected from the group consisting of: a) CD73; b) CD90; c) CD105; and d) a combination thereof;

(b) said bone marrow-derived mesenchymal stem cells possess markers selected from the group consisting of: a) LFA-3; b) ICAM-1; c) PECAM-1; d) P-selectin; e) L-selectin; f) CD49b/CD29; g) CD49c/CD29; h) CD49d/CD29; i) CD29; j) CD18; k) CD61; 1) 6-19; m) thrombomodulin; n) telomerase; o) CD10; p) CD13; q) integrin beta; and r) a combination thereof; and/or (c) is a mesenchymal stem cell progenitor cell.

23. The method of claim 22, wherein said mesenchymal progenitor cells are a population of bone marrow mesenchymal stem cells expressing STRO-1.

24. The method of claim 23, wherein said mesenchymal progenitor cells express both STRO-1 and VCAM-1.

25. The method of claim 23, wherein said STRO-1 expressing cells are negative for at least one marker selected from the group consisting of: a) CBFA-1; b) collagen type II; c) PPAR.gamma2; d) osteopontin; e) osteocalcin; f) parathyroid hormone receptor; g) leptin; h) H-ALBP; i) aggrecan; j) Ki67; k) glycophorin A; and 1) a combination thereof; and/or are positive for a marker selected from the group consisting of: a) VCAM-1; b) TKY-1; c) CD146; d) STRO-2; and e) a combination thereof.

26. The method of claim 16, wherein said bone marrow mesenchymal stem cells lack expression of CD14, CD34, and/or CD45.

27. The method of claim 16, wherein (a) said bone marrow mesenchymal stem cell express markers selected from the group consisting of: a) CD13; b) CD34; c) CD56; d) CD117; and e) a combination thereof;

(b) do not express CD10;

(c) do not express one or more of CD2, CD5, CD14, CD19, CD33, CD45, and DRII; and/or (d) express one or more of CD13,CD34, CD56, CD90, CD117 and nestin, and do not express one or more of CD2, CD3, CD10, CD14, CD16, CD31, CD33, CD45 and CD64.

28. The method of claim 16, wherein said skeletal mesenchymal stem cells express markers selected from the group consisting of a) CD13; b) CD34; c) CD56; d) CD117; and e) a combination thereof and/or wherein said skeletal muscle mesenchymal stem cells do not express CD10, CD2, CD5, CD14, CD19, CD33, CD45, and DRII.

29. The method of claim 16, wherein (a) said subepithelial umbilical cord-derived mesenchymal stem cells express markers selected from the group consisting of a) CD29; b) CD73; c) CD90; d) CD166; e) SSEA4; f) CD9; g) CD44; h) CD146; i) CD105; and j) a combination thereof;

(b) said subepithelial umbilical cord-derived mesenchymal stem cells do not express markers selected from the group consisting of a) CD45; b) CD34; c) CD14; d) CD79; e) CD106; f) CD86; g) CD80; h) CD19; i) CD117; j) Stro-1;

k) HLA-DR; and 1) a combination thereof;

(c) express one or more of CD29, CD73, CD90, CD166, SSEA4, CD9, CD44, CD146, and CD105;

(d) do not express one or more of CD45, CD34, CD14, CD79, CD106, CD86, CD80, CD19, CD117, Stro-1, and HLA-DR; and/or (e) are positive for OCT4 and/or SOX2.

30. The method of claim 1, further comprising a repeated administration of said regenerative cells and/or products derived from said regenerative cells.

\*  \*  \*  \*  \*